United States Patent [19]
Cox et al.

[11] Patent Number: 6,141,588
[45] Date of Patent: Oct. 31, 2000

[54] CARDIAC SIMULATION SYSTEM HAVING MULTIPLE STIMULATORS FOR ANTI-ARRHYTHMIA THERAPY

[75] Inventors: Timothy J. Cox, Lake Jackson; John P. Rosborough, Houston, both of Tex.

[73] Assignee: Intermedics Inc., Angleton, Tex.

[21] Appl. No.: 09/122,398

[22] Filed: Jul. 24, 1998

[51] Int. Cl.$^7$ ................................................. A61N 1/368
[52] U.S. Cl. ................................ 607/9; 128/903; 607/33
[58] Field of Search ............................ 607/9, 33, 36, 607/37; 128/903

[56] References Cited

U.S. PATENT DOCUMENTS

| | | | |
|---|---|---|---|
| 4,152,540 | 5/1979 | Duncan et al. | 174/152 |
| 4,424,551 | 1/1984 | Stevenson et al. | 361/302 |
| 4,516,579 | 5/1985 | Irnich | 128/419 |
| 4,524,774 | 6/1985 | Hildebrandt | 607/62 |
| 4,830,006 | 5/1989 | Haluska et al. | 128/419 |
| 4,880,004 | 11/1989 | Baker, Jr. et al. | 128/419 |
| 4,886,064 | 12/1989 | Strandberg | 607/18 |
| 5,010,887 | 4/1991 | Thornander | 128/696 |
| 5,333,095 | 7/1994 | Stevenson et al. | 361/302 |
| 5,342,401 | 8/1994 | Spano et al. | 607/5 |
| 5,383,912 | 1/1995 | Cox et al. | 607/32 |
| 5,406,444 | 4/1995 | Selfried et al. | 361/302 |
| 5,411,535 | 5/1995 | Fujii et al. | 607/32 |
| 5,411,537 | 5/1995 | Munshi et al. | 607/33 |
| 5,446,447 | 8/1995 | Carney et al. | 340/572 |
| 5,480,415 | 1/1996 | Cox et al. | 607/32 |
| 5,539,775 | 7/1996 | Tuttle et al. | 375/200 |
| 5,650,759 | 7/1997 | Hittman et al. | 333/182 |
| 5,676,153 | 10/1997 | Smith et al. | 128/702 |
| 5,697,958 | 12/1997 | Paul et al. | 607/31 |
| 5,814,089 | 9/1998 | Stokes et al. | 607/32 |
| 5,876,425 | 3/1999 | Gord et al. | 607/33 |

FOREIGN PATENT DOCUMENTS 0266907   11/1988   European Pat. Off. .

OTHER PUBLICATIONS

Biomedical Instrumentation & Technology/Medical Device Research Report; Nerve Implant Could Provide Hope for Paralysis Patients; Jul./Aug. 1997; 2 pages.

Tracy Cameron, Gerald E. Loeb, Raymond A. Peck, Joseph H. Schulman, Primoz Strojnik and Philip R. Troyk/IEEE Transactions on Biomedical Engineering, vol. 44, No. 9; Micromodular Implants to Provide Electrical Stimulation of paralyzed Muscles and Limbs; Sep. 1997; 10 pages.

*Primary Examiner*—Carl H. Layno
*Attorney, Agent, or Firm*—Schwegman, Lundberg, Woessner & Kluth, P.A.

[57] ABSTRACT

A medical system comprising a control device (referred to as a "planet") and a plurality of sensing and stimulating devices (referred to as "satellites") is disclosed. The satellites are relatively small devices that can be thoracoscopically attached to an exterior surface of the heart. The planet can be implanted if desired or, alternatively, externally retained. The planet is capable of wirelessly communicating (i.e., without a direct electrical connection) to each satellite. The planet individually commands each satellite to deliver pacing energy to the heart. Additionally, each satellite is capable of determining when a sense event has occurred at the site of that satellite and transmitting an encoded signal to the planet indicating that a sense event has occurred, along with an identifying code indicating to the planet which satellite detected the sense event. The planet processes the encoded signals received from the network of satellites, assigns time values to each satellite when that satellite detects a sense event, compares the time values to a template of normal values, and determines if an arrhythmia has occurred if the time values do not match the template. Further, the planet selects and implements an appropriate pacing protocol to terminate the arrhythmia. The satellites derive their needed power from signals received from the planet via the wireless communication path.

43 Claims, 12 Drawing Sheets

CARDIAC SIMULATION SYSTEM HAVING MULTIPLE STIMULATORS FOR ANTI-ARRHYTHMIA THERAPY

BACKGROUND OF THE INVENTION

1. Field of the Invention

The present invention relates generally to cardiac stimulator and arrhythmia therapeutic devices, and more specifically to an anti-arrhythmia device including multiple stimulators. Still more particularly, the invention relates to a medical device including a planet electronics assembly and an array of implantable satellite stimulators controlled by and receiving power, partly or wholly, from the planet via wireless communications links,

2. Background of the Invention

The human heart pumps blood to the lungs to absorb oxygen and then pumps the oxygenated blood to the tissues of the body. After the oxygen is removed from the blood by the tissues, the oxygen-depleted blood returns to the heart and the process repeats itself. The heart comprises four chambers-two atria and two ventricles. Once the atria fill with the blood, the atria contract forcing blood into the ventricles. After the ventricles fill with blood, the ventricles, in turn, contract forcing blood to the lungs (from the right ventricle) and to the rest of the body (from the left ventricle).

The chambers of the heart contract in response to electrical signals or "wavefronts." In the normal human heart, a collection of cardiac cells referred to as the "sinus" node (or "sinoatrial node") constitutes the primary natural pacemaker by which rhythmic electrical excitation is developed to cause the chambers to contract. The cardiac impulse arising from the sinus node is transmitted to the two atrial chambers (or atria) at the right and left sides of the heart. The impulse from the sinus node is transmitted to the ventricles through the atrioventricular node. The transmitted impulse causes the ventricles to contract. The cycle of events during which an electrical impulse is conducted through the heart causing contraction of the atria followed by contraction of the ventricles is referred to as a "cardiac cycle."

Disruption of the heart's natural pacemaking system as a result of aging, disease or surgical intervention is commonly treated by artificial cardiac pacing, by which rhythmic electrical discharges are applied to the heart at a desired rate from an artificial pacemaker. An artificial pacemaker (or "pacer" as it is commonly labeled) is a medical device which typically senses electrical impulses and delivers electrical pulses to one or more electrodes that are implanted adjacent to or in the patient's heart in order to stimulate the heart to contract at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Conventional pacers thus include an electronics assembly housed in a hermetically sealed enclosure, and one or more leads which connect the pacer directly to the heart tissues to be stimulated and sensed. By using a lead, which may be, for example, 18–30 inches in length, the electronics assembly can be implanted in a suitable area of the body, commonly the upper thorax. One end of the lead connects to the pacer, while the other end of the lead, referred to as the "distal" end, is attached to an interior surface of one of the chambers of the heart. One or more electrodes typically are disposed at the distal end of the lead through which electrical pulses are delivered to the heart at the site of the electrodes and/or from which sensing occurs. During implantation of conventional pacer systems, it is a common procedure for the physician to insert a stiff wire ("stylette") through the center of the lead and then to "snake" the lead through a predetermined path to the heart. Often the leads are implanted by guiding them through blood vessels into one or more chambers of the heart. The leads typically pass through valves that separate the atrial from the ventricular chambers.

In addition to supplying stimulating pulses to the heart, an important function performed by most modern pacemakers is sensing the electrical activity of the heart. The term "sensing" means to monitor the intrinsic electrical activity of the heart which normally precedes cardiac contraction. Conventional pacers thus include monitoring (or "sense") circuitry, such as amplifiers and filters, to process the electrical signals detected by the electrodes implanted in the heart. The processed signals are then compared to preset threshold signals used to determine whether cardiac function is within acceptable bounds. If the sense circuitry determines that the patient's heart is not beating in an acceptable manner, the pacer may provide an electrical pulse or typically, a sequence of pulses, through the lead and electrodes to artificially stimulate the heart to beat in a predetermined manner.

Although leads have been used for many years in conjunction with implanted pacemakers and defibrillators both to stimulate the heart to beat as well as to sense the electrical activity of the heart, the use of leads is not problem free. For instance, the implantation avenues available for leads to be routed to and through the heart may be limited by the lumenal diameter of the vessels leading to the heart or by valves in the heart. Chronic fixation of the lead may be influenced by anchorage available (e.g. trabeculas). Further, introduction of leads into the right side of the heart is usually preferred for implantation of pacer leads because of the reduced risk of blood loss, as the pressures in the right cardiac chambers are markedly lower than the pressures in the left cardiac chambers. Thus, for these practical reasons, a physician typically only implants the leads in a relatively few preselected sites in the heart. These sites, however, are not necessarily the optimal sites for sensing the electrical activity of the heart, but are chosen as a compromise between the complications described above and the patient's cardiac problem. Rather than monitoring the electrical activity in the right ventricle, monitoring the left ventricle's electrical activity, for example, might be preferred instead.

Additionally, it may desired to sense electrical activity at three, four, or more sites in the heart. Some pacers may be implanted with four leads permitting sensing at four different sites in the heart. Four leads may be difficult to implant as they occupy a relatively large volume in the blood vessels through which they are passed and sometimes have to be steered along circuitous routes. Further, it is becoming increasingly desirable to sense at more locations in or on the heart than is possible with conventional pacer-lead combinations. It would thus be highly beneficial to have a stimulation and sensing system that provides the diagnostic and therapeutic functions provided by conventional cardiac stimulators yet which employs fewer interconnecting leads, than required by conventional devices, or which can function without using any leads.

Two broad categories of arrhythmias include "bradycardia," which is characterized by a relatively slow heart rhythm, and "tachycardia," which is characterized by a relatively fast rhythm. It is generally known that slow "depolarization wavefront" propagation across the heart such as that caused by conduction block, gives rise to bradycardic conditions. The term "depolarization wavefront" refers to the spatial distribution of electrical charge across the heart as the heart contracts. The pacer "senses" the "depolarization wavefront" as it passes the site of electrodes. Throughout this disclosure "depolarization wavefronts" (or simply depolarization waves) is used synonymously with "sense events."

It is also generally known that tachycardic conditions arise from circus motions which are "depolarization wavefronts" which move around localized regions of cardiac tissue, such as that described in a book by W. A. Tacker and L. A. Geddes entitled "Electrical Defibrillation," CRC Press, 1980. Several circus motions may occur simultaneously, giving rise to chaotic, rotor motion characteristic of life-threatening fibrillation. Present means to control or inhibit these conditions generally require delivering enough energy via the lead electrodes to "capture" a critical volume of repolarizable tissue all at once. In so doing, a major portion of the cardiac tissue of the affected heart chamber is induced into a non-polarizable, refractory, state from which it can recover by means of artificial or natural pacing. Because brady and tachycardia often are arrhythmias occurring in a localized area of the heart, some conventional pacers and defibrillators are unable to effectively and consistently detect the onset of these conditions because of the limited number of leads and the compromise in lead locations. It would thus be desirable to be able to sense the heart's electrical activity at numerous (i.e., two or more and preferably four or more) locations within the heart.

For the foregoing reasons, a cardiac stimulator that reduces or eliminates the problems associated with conventional pacers that require leads is needed. Such a stimulator would reduce the number of leads, or eliminate the use of leads altogether.

SUMMARY OF THE INVENTION

Accordingly, there is provided herein a medical system comprising a control device (referred to as a "planet") and a network of remote sensing and stimulating devices (referred to as "satellites"). The satellites are relatively small devices that can be thoracoscopically attached to the exterior surface of the heart. The planet can be implanted if desired or, alternatively, retained on or attached to the outside of the patient's body. The planet is capable of wirelessly communicating (i.e., without a direct electrical connection) to each satellite. Each satellite is configured with a unique identification code and the planet selectively communicates with each satellite individually by using the appropriate code. The planet commands each satellite individually to deliver pacing energy to the heart. Additionally, each satellite is capable of determining when a sense event has occurred at the site of that satellite, and transmitting to the planet both an encoded signal indicating that a sense event has occurred and an identifying code identifying which satellite detected the sense event.

Each satellite includes a pair of electrodes, a sense amplifier, and a communications device for communicating with the planet. The satellites may further include a battery to provide the needed electrical power to operate the satellites' circuitry. Preferably, however, all needed electrical power required by the satellites can be derived from electromagnetic signals transmitted from the planet to the satellites. Each satellite further includes a rectifier and regulator to condition the signals received from the planet into a form that can be used to power the satellite's electronics. Each satellite preferably also includes a stimulus storage device that stores electrical energy for subsequent delivery to the heart via the electrodes. The satellite may include a comparator that, along with the sense amplifier, monitors the electrical signals detected by the satellites' electrodes to determine if a sense event has occurred. The satellites may also include a receiver data encoder/decoder to generate signals to be transmitted to the planet and to decode signals received from the planet. Upon receipt of a command from the planet indicating that the satellite should pace the heart, the receiver data decoder/encoder asserts a control signal to direct the stimulus storage device to deliver its stored electrical energy through the electrodes to the heart. The satellites' electrodes preferably include a barbed or corkscrew projection for attaching the satellites to the heart and establishing electrical contact with the cardiac tissue.

The planet comprises the central control unit for controlling the plurality of satellites and preferably includes a CPU, RAM and ROM memory, a clock for generating a periodic timing signal, a counter for receiving the periodic timing signal, a communications device, an antenna, and may include a body activity sensor and other electronics to provide communication with the planet. The planet can selectively transmit electromagnetic energy encoded with commands on an individual basis to each satellite to command the satellite to pace the cardiac tissue to which the satellite is coupled. The planet can also receive signals from each satellite indicating that the satellite has detected the occurrence of a depolarization wavefront. The planet includes a disposable or rechargeable battery that provides electrical power for the planet's circuitry, as well as providing electrical energy to operate the satellites. Accordingly, the electromagnetic energy transmitted from the planet to the satellites is converted to electrical current to be used to power the circuitry in the satellites. Thus, the electromagnetic energy transmitted from the planet to the satellites serves two purposes—transmission of configuration data and commands to control the operation of the satellites, and transmission of energy to power the satellites' electronics.

The planet's counter counts cycles of the periodic timing signal from a clock to measure time. The CPU in the planet is capable of resetting the counter and preferably resets the counter at, or near, the beginning of a cardiac cycle. Then, as each satellite in the network reports the occurrence of a sense event to the planet, the CPU reads the current count value from the counter and assigns the current count value to the satellite that reported a sense event. The current count value is indicative of the period of time that has elapsed from the beginning of the cardiac cycle to the time that the satellite detected a sense event. This process is repeated for all satellites that report sense events during a cardiac cycle. In this manner, the planet can determine which satellites detect sense events and when each satellite detects its sense event during each cardiac cycle. Using this information, the planet can determine if a patient is experiencing an arrhythmia, characterize the arrhythmia, and initiate an appropriate anti-arrhythmia therapy.

During implantation of the planet and satellite network, the physician may use an external programmer unit (EPU) to initialize the network. The EPU can communicate with the planet and, if desired, with the satellites. During the initialization process, which preferably occurs while the patient is experiencing normal sinus rhythm, the surgeon uses the EPU to inform the planet how many satellites have been implanted and which satellite in the network will first detect a sense event during each cardiac cycle. With this information stored in the planet's memory, the planet's CPU resets its counter when it receives a sense event signal from the satellite that should first detect a sense event signal during each cardiac cycle. The planet then reads the counter each time a subsequent sense event signal is received from the other satellites in the network and stores these count values in the planet's memory. These count values establish a template of normal count values for that patient during normal cardiac rhythm. After initialization is completed, the planet's CPU resets its counter (or its output may be latched in a separate register and the counter is kept running) each time the planet receives a sense event signal from that satellite and assigns the counter's output count value to each satellite that transmits a sense signal to the planet. The CPU in the planet then compares the assigned count values to the template stored in its memory for determining whether the patient is experiencing an arrhythmia.

Thus, the present invention comprises a combination of features and advantages that enable it to substantially advance the art by providing a network of implantable medical devices that communicate with one host unit and electrically stimulate the heart without the risks and disadvantages associated with the use of the interconnection wire leads. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

A better understanding of the present invention can be obtained when the following detailed description of the preferred embodiments is considered in conjunction with the following drawings, in which.

DETAILED DESCRIPTION OF PREFERRED EMBODIMENTS

Figure 1:
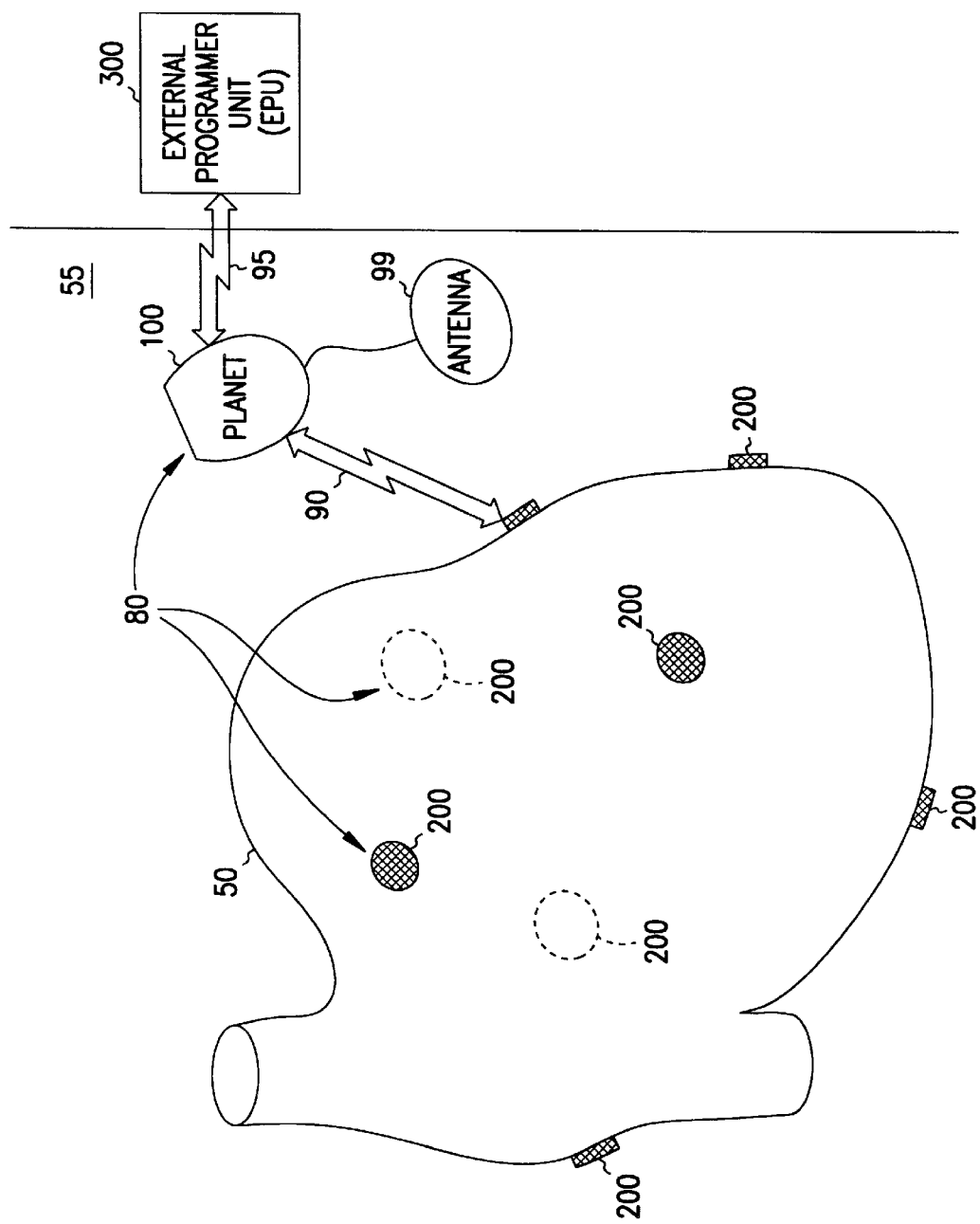
FIG. 1 diagrammatically shows an implantable medical device network including a "planet" and a plurality of "satellites" constructed in accordance with the preferred embodiment of the invention.

Referring now to FIG. 1, an implantable medical system 80, constructed in accordance with the preferred embodiment, includes a central electronics assembly 100 and one or more, and preferably two or more, remote sensing and stimulating units 200. For purposes of this disclosure, the central electronics assembly 100 is referred to as the "planet" and the remote sensing and stimulating units 200 are referred to as "satellites." The planet and satellites preferably are implanted into the body 55 with the satellites preferably attached to a human heart 50. The satellites each communicate with the planet via wireless communication links 90 (one shown) through which data is transferred from the satellites to the planet for processing. In addition, commands and configuration data are transferred via communication links 90 from the planet to each satellite individually. The planet 100 may also communicate with an external programmer unit (EPU) 300 located externally to the body 55 via a communication link 95.

As shown in FIG. 1, the implantable medical system 80 operates to assist the heart to beat correctly. It is contemplated, however, that the planet/satellite architecture may be used in other types of implantable medical devices, such as nerve stimulators and drug delivery devices. For simplicity, the preferred embodiment of the invention, as shown in FIGS. 1–13 will be described as representing a cardiac sensor and stimulator, and referred to as a pacemaker (or simply "pacer") network. Pacer network 80 is particularly well-suited for detecting cardiac arrhythmias, such as bradycardia (slow heart rate), tachycardia (fast heart rate), and fibrillation (chaotic rate), and then implementing a suitable pacing therapy to terminate the arrhythmia.

Notably, implantable pacer network 80 permits planet 100 to communicate data and commands with the satellites without the use of leads as typically required for present day pacemakers. The satellites 200 may be implanted on the outer surface of the heart using thoracoscopic or other suitable implantation techniques. The antenna 99 of planet 100 preferably is implanted in a location to permit communication with the satellites as well as the EPU 300. Because the planet communicates with each satellite without a direct physical connection, the planet alternatively may be located external to the body 55. In this latter configuration, the planet may be strapped, or otherwise held in close proximity, to the patient's chest so as to permit effective communication with the implanted satellites.

The pacer network 80 depicted in FIG. 1 may include any number of satellites. The pacer network includes at least one satellite, preferably at least two, and more preferably still at least four satellites. As shown in FIG. 1, the pacer network 80 is illustrated with eight satellites, but may include more than eight if desired. Each satellite is capable of communicating to the planet 100 data representative of the electrical activity of the heart at the site of that satellite. Also, the planet can command each satellite to provide an electrical pulse to the heart (i.e., pace the heart) at the site of the satellite to cause the heart muscle to contract at that location. Because pacer network 80 does not include leads, the problems associated with leads noted above are avoided and the pacer network may include satellites to sense and pace the heart at more locations than possible with pacemakers that include leads. Accordingly, the pacer network 80 may provide more effective diagnostic and therapeutic benefit than previous pacemakers. The benefits of pacer network 80 to treat bradycardic, tachycardic, fibrillation, and other arrhythmic conditions will become apparent particularly once FIGS. 9–13 and the associated text are reviewed.

Planet 100 will now be described with reference to FIGS. 2–4. The following detailed description describes the preferred embodiment for implementing the underlying principles of the present invention. One skilled in the art should understand, however, that the following description is meant to be illustrative of the present invention, and should not be construed as limiting the principles discussed herein. In addition, certain terms are used throughout the following description and claims to refer to particular components. As one skilled in the art will appreciate, medical device companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection or through an indirect electrical connection via other devices and connections.

Figure 2:
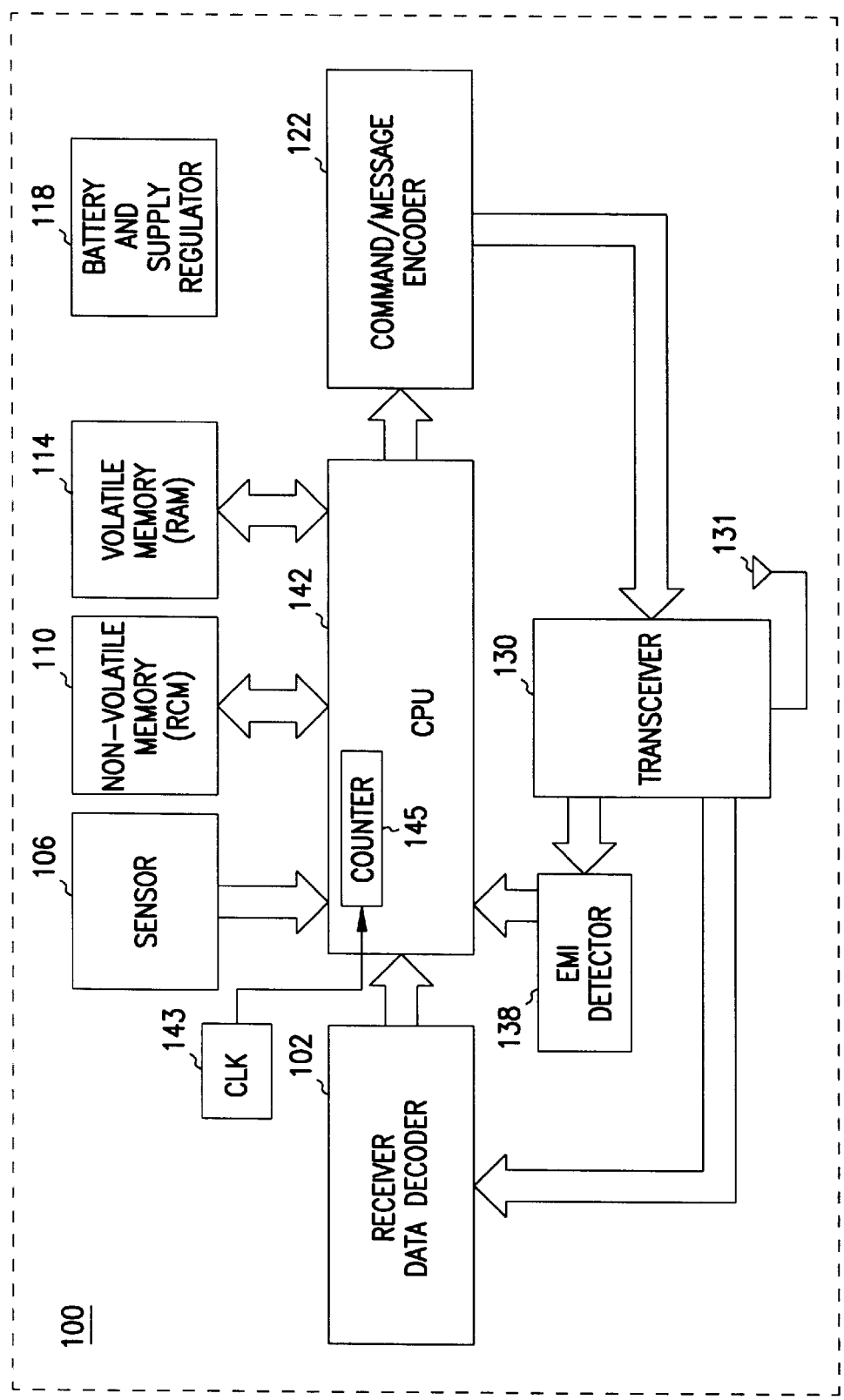
FIG. 2 is a block diagram showing the interconnection between the various components and circuitry of the planet of FIG. 1.
Figure 3:
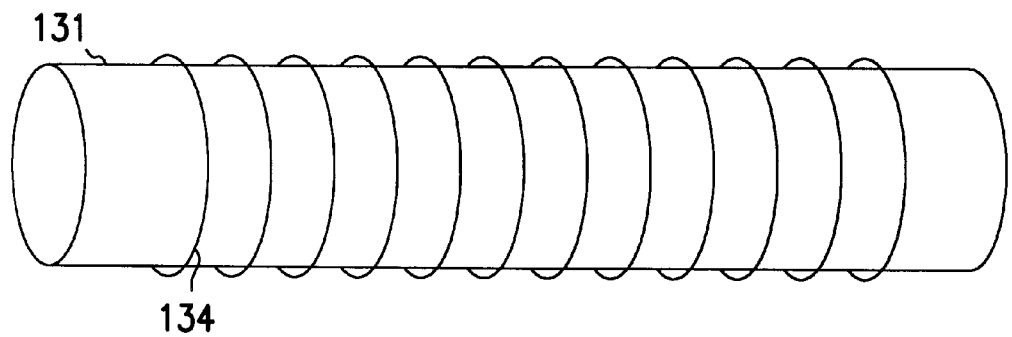
FIG. 3 is a view of one embodiment of an antenna used in conjunction with the planet of FIG. 1.

Referring now to FIG. 2, the planet 100 generally includes a receiver data decoder 102, a sensor 106, a non-volatile memory (e.g., ROM) 110, a volatile memory (e.g., RAM) 114, a battery and supply regulator 118, a command/message encoder 122, a transceiver 130, an antenna 131, an electromagnetic interference (EMI) detector 138, and a central processing unit (CPU) 142. The planet also includes a clock generator 143 that provides a periodic timing signal to a counter 145 which may be included as part of CPU 142. Other components may be included in planet 100 as desired.

The CPU 142 preferably includes any suitable type of commercially available processor or may be a custom design. The CPU controls the operation of planet 100. Generally, the CPU 142 processes data received from the satellites 200 via the transceiver 130 and antenna 131, and receiver data decoder 102. The CPU 142 also initiates the transmission of commands to each satellite individually by conveying a message to the command/message encoder 122 which, in turn, provides an encoded message to be transmitted through antenna 131 via transceiver 130. The CPU also receives inputs from the sensor 106, ROM 110, RAM 114, EMI detector 138, and clock 143. The non-volatile memory (ROM) 110 is used to store configuration and program code for execution by CPU 142. Volatile memory (RAM) 114 is used as "scratch-pad" memory for storing data used by CPU 142.

The battery and supply regulator 118 preferably provides electrical power for the planet's circuitry. The construction of the battery preferably uses a chemistry known to one skilled in the art. For example, the battery may include a disposable lithium iodide cell, but may employ rechargeable cells as well. The use of a rechargeable battery permits the planet's size to be smaller than if a non-rechargeable battery is used because a disposable battery need not hold as much charge as a disposable battery. A rechargeable battery, however, requires periodic recharging by an external device. An exemplary rechargeable battery may employ a lithium-ion chemistry. If a rechargeable battery is used, the planet preferably includes a coil of wire to capture inductively-coupled energy from an external device such as EPU 300. An exemplary technique for providing energy into an implanted medical device is described in U.S. Pat. No. 5,411,537, assigned to Sulzer Intermedics and incorporated herein by reference.

The EMI detector 138 couples between the transceiver 130 and CPU 142. The EMI detector 138 receives the signal detected by the antenna 131 and processes that signal to determine when the patient is experiencing a relatively high level of electromagnetic inference such as that generated by a metal detector in an airport, for example. Such EMI may be detected by the satellites 200 and may be confused with electrical signals generated by the heart 50. The EMI detector 138 sends a signal to the CPU 142 when radiated interference within the frequency range used for communication with the satellites is detected. The EMI detector may further include processing to discriminate wanted signals originating from the satellites from unwanted interference. The EMI detector detects the presence of electromagnetic interference using any conventional technique such as that described in U.S. Pat. Nos. 4,516,579, 5,010,887, or 5,697,958, incorporated herein by reference. Once detected, the EMI detector may inform the CPU 142 that interference is present, or may inform the CPU which frequencies are affected. In the former case, the CPU preferably correlates the sensed signals from several satellites sent to the planet 100. In the latter case, the CPU may choose not to communicate or send energy to the satellites having frequencies within the band of frequencies associated with the interference. The CPU may choose to indicate to the patient that diagnosis and therapy are jeopardized by the presence of EMI, by means of a muscle twitcher, such as that disclosed in U.S. Pat. No. 4,140,131 or 5,628,776 or an audible device, such as that disclosed in U.S. Pat. No. 4,614,192. Alternatively, the CPU may command the satellites to cease sensing and commence asynchronous pacing, such as is commonly referred to in conventional pacemakers as "noise" mode or "interference" mode.

The satellites 200 transmit signals via wireless communication links to the planet 100. The transmitted signals are detected by the planet's antenna 131 and demodulated in transceiver 130. The antenna 131 preferably includes a coil of wire, parallel plates, dipoles or other suitable types of antennae to launch or capture electromagnetic energy. Antenna 131 may also be implemented as other types of transducers, such as ultrasonic (piezoelectric) devices. The transceiver 130 includes modulators, demodulators and splitters for processing the signal from the antenna 131. The wireless communication technique can be any suitable technique such as that described in U.S. Pat. No. 5,539,775.

The output signal from the transceiver 130 also is provided to the receiver data decoder 102. The demodulation method used by transceiver 130 is an appropriate method given the communication methodology implemented via the pacer network 80 for transmitting signals between satellites and the planet, such as frequency demodulation, amplitude demodulation or phase shift keying demodulation. The demodulated signal from transceiver 130 is then coded by receiver data decoder 102 and provided in digital from to CPU 142 over a digital bus.

Referring still to FIG. 2, the master clock 143 generates a periodic timing signal which is provided to counter 145.

Counter 145 may be included as part of the CPU 142 or may be a discrete device coupled to the CPU. The counter 145 counts cycles of the periodic timing signal generated by clock 143. The CPU can read the counter to determine the current count value. For example, if the clock signal is a 1000 Hz (1000 cycles per second) and a counter counts 500 cycles of the clock signal, the CPU will then know that the counter has counted for one-half of a second. The counter preferably is implemented as a "count up" counter and provides an output count value that begins with 0 and increments by 1 for each cycle of the periodic timing signal. Preferably, the CPU 142 can reset the counter 145 to begin counting again from 0.

In operation, each satellite 200 transmits a signal to the planet 100 when the satellite detects a sense event. The CPU uses the count value read from counter 145 to determine when the sense event (reported by a satellite) has occurred during each cardiac cycle. Upon receiving a sense event signal from a satellite, the planet 100 reads the current count value from counter 145 to determine how much time has elapsed since the counter was last reset. The CPU 142 may have been programmed to reset the counter 145 at or near the beginning of each cardiac cycle and thus, the count value read by the CPU is indicative of when the sense event occurred during the cardiac cycle. Alternatively, the count value may be latched in a register (not shown) while the counter continues.

During implantation, and explained in detail below with reference to FIG. 8, the physician affixes one or more satellites 200 to the exterior or interior surface of the heart. These sites selected for attaching the satellites depend on the particular cardiac problem suffered by the patient. As the depolarization wavefront propagates across the surface of the heart during a cardiac cycle, each satellite will detect the presence of the depolarization wave as it passes through the tissues to which the satellite is affixed. Based on the implantation site of the satellites selected by the physician, the physician will know which satellite should first detect the depolarization wave during each cardiac cycle. Using the EPU 300, the physician communicates to the planet 100 which satellite should first detect a sense event during each cardiac cycle. In accordance with the preferred embodiment of the invention, the CPU 142 resets the counter 145 when that particular satellite reports the occurrence of a sense event.

When the planet 100 receives a sense signal from the satellite 200 that should first detect a depolarization wave during each cardiac cycle, the CPU 142 resets the counter 145 and assigns a count value of zero for that satellite. Then, upon receiving a sense event signal from another satellite in the network, the CPU reads the counter and assigns the current count value to that satellite. The count value assigned to a satellite is thus the time that has elapsed since the first satellite reported the occurrence of a sense event to the planet. The CPU 142 preferably stores in RAM memory 114 the count values assigned to the array of satellites. As will be described in greater detail with respect to FIGS. 8-13, the planet 100 stores a template of counter time values in the RAM memory 114. This template is indicative of the normal timing of a depolarization wave for the patient during normal cardiac rhythm. The planet 100 compares the timing count values for each cardiac cycle against the count values in the template to determine if the patient's heart is experiencing an arrhythmia. Further, the planet 100 can determine which type of arrhythmia the patient is experiencing based on a comparison with the template.

Thus, the CPU processes the data provided by the satellites, and, based on principles described below, selects an appropriate pacing therapy, if one is needed. The chosen therapy may be antitachycardia, antibradycardia, or defibrillation. In the case of tachycardia, the sensor 106, which may be any suitable sensor such as, for example, an accelerometer, impedance sensor, pressure transducer, or blood flow transducer, is interrogated by the CPU. If the tachycardia is found to be produced by physical exertion or exercise, then antitachycardia therapy is not provided to the patient's heart. Once selected, the planet's CPU uses the command/message encoder 122 to encode digital commands that are modulated in the transceiver 130. The transceiver 130 then delivers the modulated signal to the antenna 131 for transmission to a satellite 200. The planet can command each satellite individually and thus encodes a satellite identifier into the transmitted signal. Each satellite 200 is programmed prior to implantation with a unique identification code and only the satellite with a matching identification code will accept and respond to the planet's command. The satellite identification codes are also used by the satellites when transmitting data to the planet so that the planet will know to which satellite the data pertains.

The antenna 131 may be located in the enclosure of the planet, or located remotely from the planet, endocardially, epicardially, or extracorporeally. One example of an intracorporeal antenna has the form of a long, insulated, flexible cylinder having a diameter preferably no larger than conventional defibrillation and pacing leads. Two exemplary embodiments of antenna 131 are shown in FIGS. 3 and 4. First with respect to FIG. 3, the antenna preferably is constructed so that the distributed capacitance from the conductor to the surrounding body tissue is larger than the distributed capacitance between each turn of the winding 134. The radio frequency (RF) current is thereby encouraged to exit the coil and return via tissue to a reference (ground) electrode which may be the metal enclosure of the planet. If desired, two or more antennas oriented at angles to one another may be used in concert to ensure proper communication with all satellites.

Figure 4:
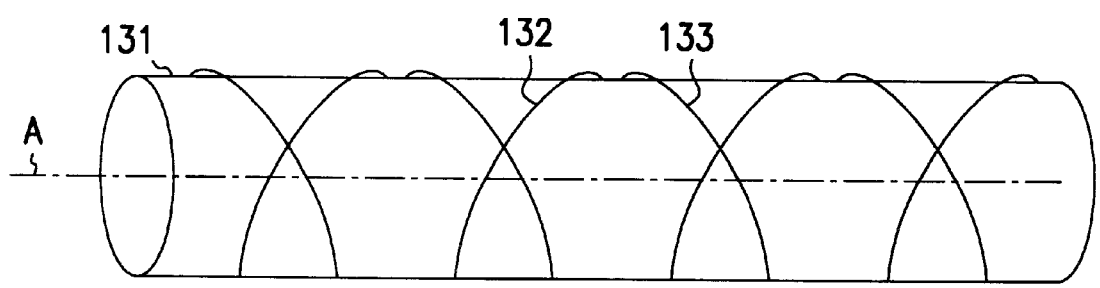
FIG. 4 is a view showing an alternative embodiment of the antenna used in conjunction with the planet of FIG. 1.

The alternative embodiment of antenna 131 shown in FIG. 4 preferably comprises two spirally wound loops 132 and 133 displaced orthogonally from each other. For this embodiment, the distributed capacitance is also larger between the antenna and the surrounding body tissue than between the turns of the windings 132, 133. Loop 132 forms one continuous winding provided with an RF current that is separate from the current flowing in loop 133, which is also one continuous winding. The magnetic fields produced by the two windings 132, 133 are orthogonal, and therefore mutual coupling is minimized. In addition, the currents in the two windings can be in-phase or out-of-phase in order to produce currents in the tissue that are not parallel to the axis A of the antenna. Antenna 131 preferably has a direction of highest energy radiation per unit solid angle that is not co-axial with axis A.

Figure 5:
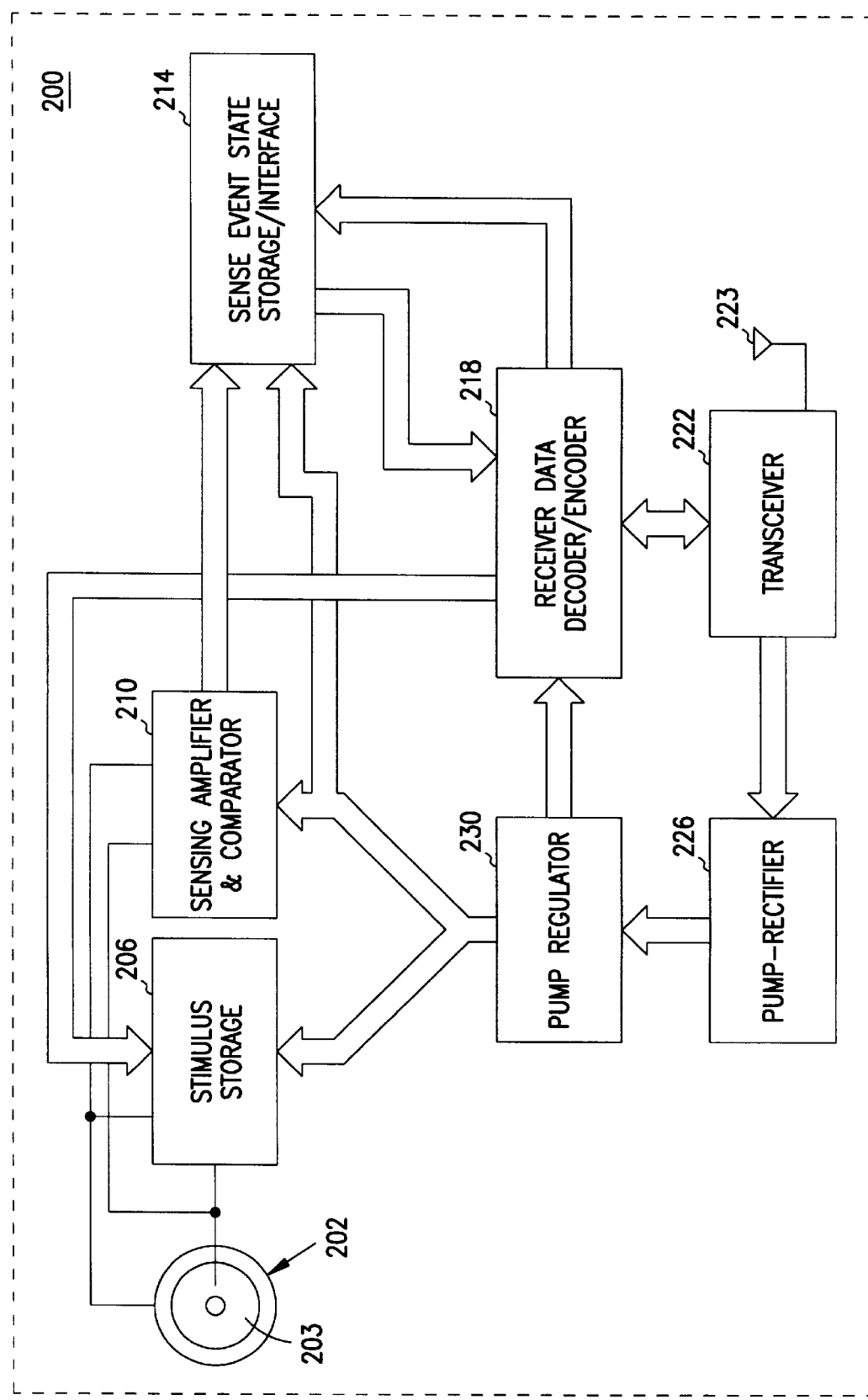
FIG. 5 is a block diagram showing the interconnection between the various components and circuitry of a satellite of FIG. 1.
Figure 15:
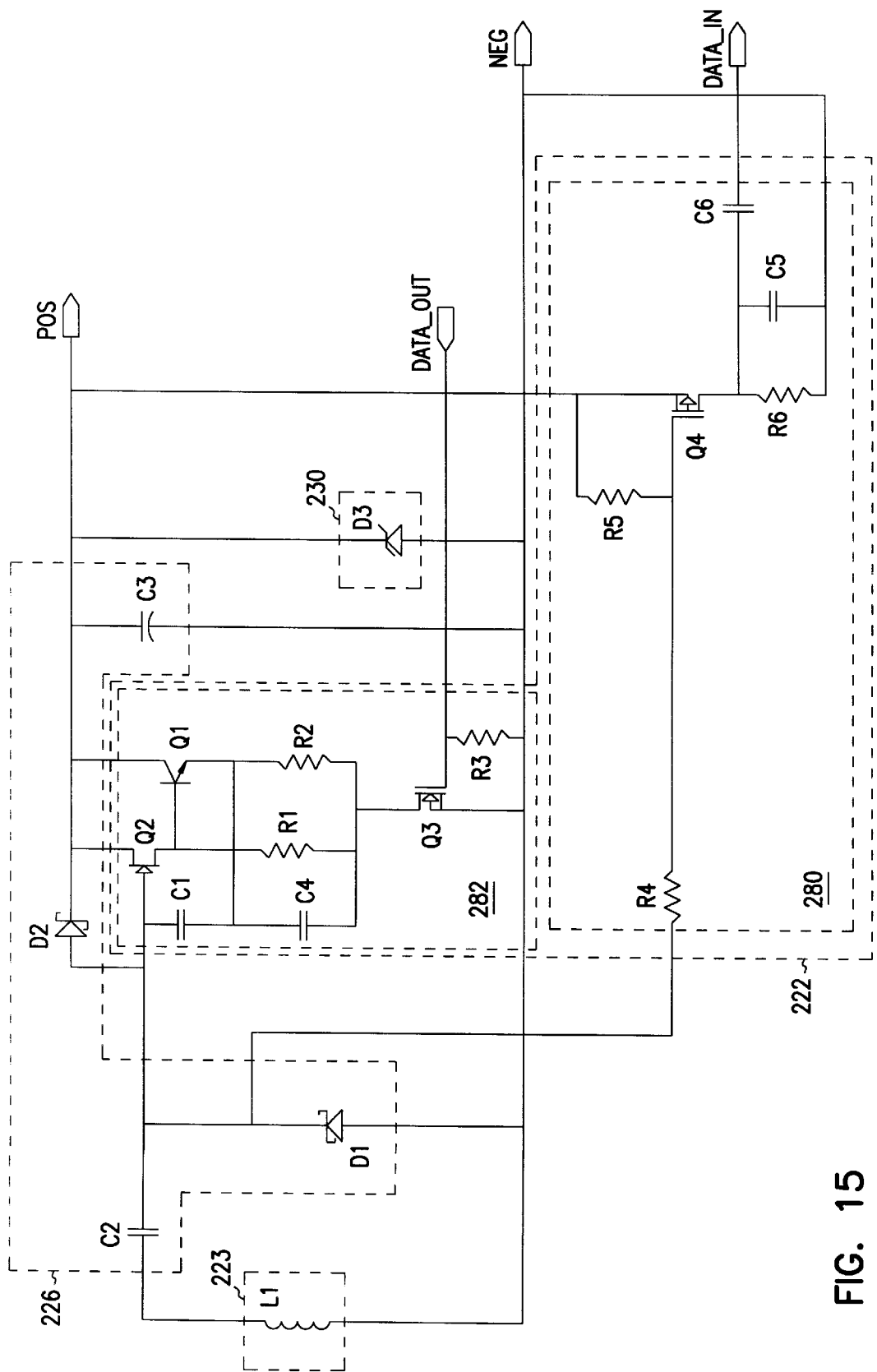
FIG. 15 is a detailed schematic diagram of a pump rectifier regulator and transceiver of the satellite of FIG. 5.
Figure 16:
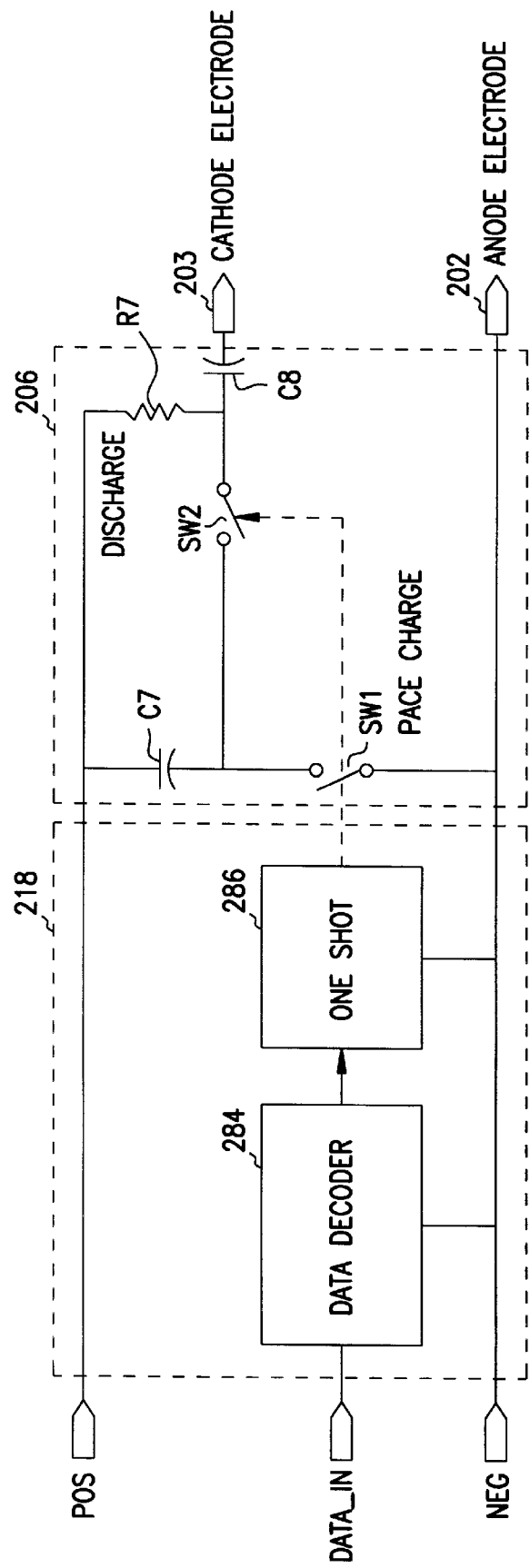
FIG. 16 is a detailed block diagram of receiver data decoder/encoder and stimulus storage of the satellite of FIG. 5.
Figure 17:
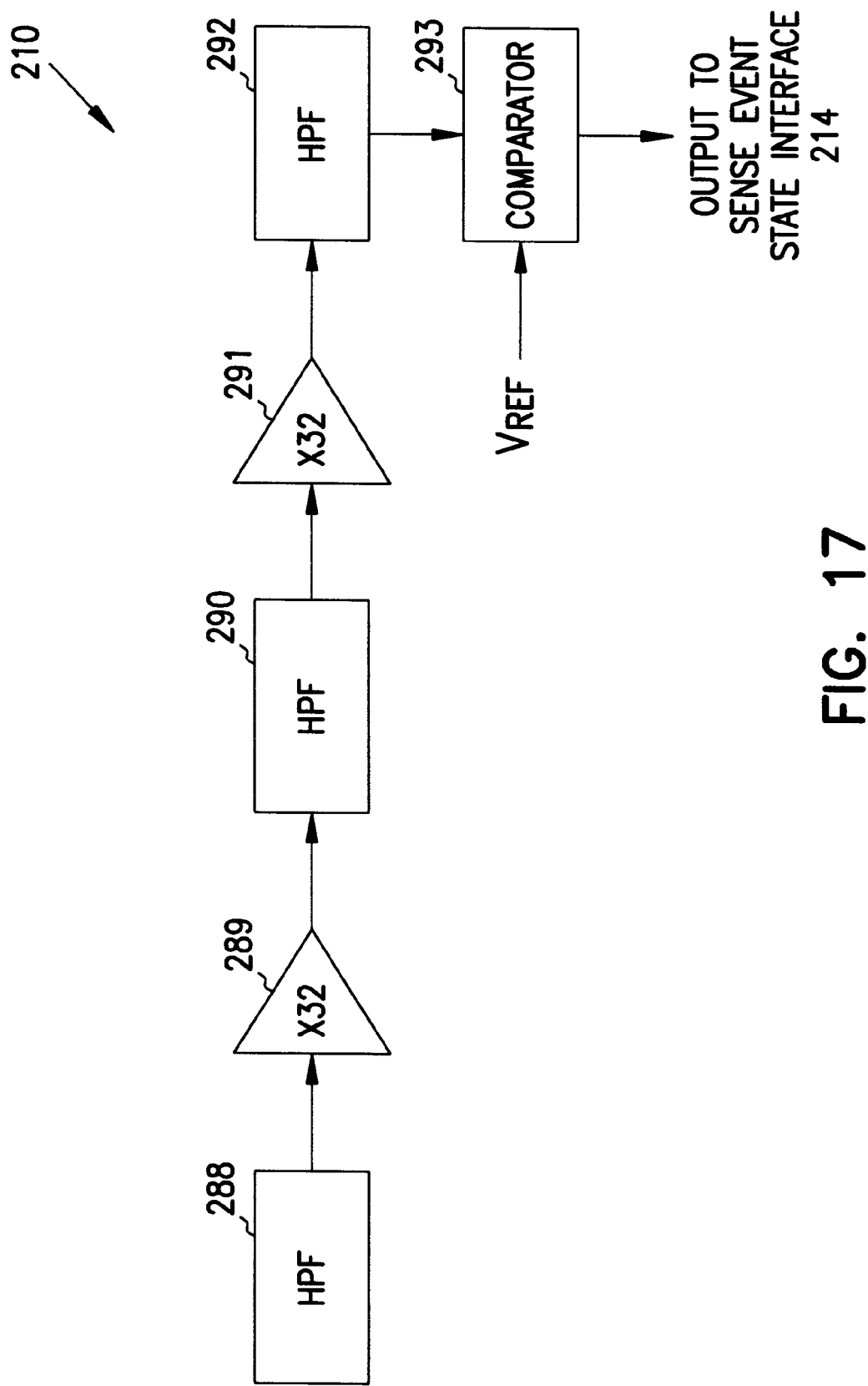
FIG. 17 is a block diagram of the amplifier and comparator of the satellite of FIG. 5.

A block diagram of a single satellite 200 is depicted in FIG. 5 with more detailed block diagrams included in FIGS. 15–17. More than one satellite may be used in the pacer network 80 and each satellite is constructed the same or similar to the satellite depicted in FIG. 5. As shown in FIG. 5, satellite 100 preferably includes a pair of electrodes 202 and 203, a stimulus storage unit 206, a sensing amplifier and comparator logic 210, a sense event state storage and interface 214, a receiver data decoder/encoder 218, a transceiver 222, an antenna 223, a pump-rectifier 226, and a pump-regulator 230.

Although a battery (not specifically shown) could be used to provide electrical power for the satellite circuitry, it is preferred that electrical power for operating the satellites' components be derived from the electromagnetic energy received from the planet. Alternatively, some of the electromagnetic energy could be used to recharge a battery if provided in each satellite. The transceiver 222 and antenna 223 receive electromagnetic energy from the planet on which encoded data may be superimposed. The received energy is rectified by the pump-rectifier 226 and regulated by the pump-regulator 230. The pump regulator 230 uses the signal received from the antenna 233 to supply a constant voltage to the other circuits of the satellite when the energy stored in the pump regulator has reached a threshold value. Alternatively, the pump-regulator may comprise a constant voltage reference device in order to stabilize sensing and stimulus storage. Without a battery for a power source in each satellite, the pacer network 80 will have a reduced risk of leakage of toxic contaminants into surrounding body tissue. Further, unlike prior medical devices that include batteries, the satellites will not have to be replaced when a power source becomes depleted.

The pump-rectifier 226 and pump regulator 230 process the electromagnetic signal normally received by the antenna 223. Thus, the signal received from the planet serves two purposes—(1) transfer of commands and configuration data, and (2) transfer of energy for powering the satellites' electronics. Accordingly, even if the planet does not need to communicate commands or configuration data to a satellite, the planet may nevertheless transmit a signal to the satellite 200 simply to keep the satellites' electronics active. Accordingly, the planet 100 may communicate briefly with each satellite in the network 80 one at a time to ensure that all satellites 200 are active and sensing for depolarization waves.

FIG. 15 is a detailed schematic illustrating the transceiver 222, antenna 223, pump-rectifier 226, and pump-regulator 230 in greater detail. Communication signals from the planet 100 are induced across antenna coil L1 preferably in the form of a radio frequency (RF) voltage. Alternatively, planet 100 and satellites 200 can be configured to transmit non-electromagnetic energy, such as sonic or ultrasonic energy using piezoelectric transmitters and receivers. This induced voltage is then rectified and pumped by capacitor C2 and diodes D1 and D2 into a higher DC voltage across capacitor C3. The zener diode D3 (which comprises the pump-regulator) preferably prevents excessive voltage from "POS" to "NEG". The POS to NEG voltage is the DC voltage supply to the rest of the satellite's electronics. While energy is being pumped in, transistors Q1, Q2, Q3, and Q4 preferably are inactive. Transistor Q4 preferably is prevented from switching on by having a source terminal voltage lower than that of its gate, due to the forward voltage drop across diode D2.

The transceiver 222 generally comprises a transmitter 282 and a receiver 280. A command is sent to the satellite preferably by causing brief breaks in the transmission. This causes the steady state positive voltage at the cathode of diode D1 to fall, and diode D2 blocks the DC voltage on capacitor C3. Transistor Q4 then switches on, causing the voltage across resistor R6 to rise, which is sensed at the DATA_IN line. Message encoding may be in terms of number of pulses in one sequence or the timing from pulse to pulse, at DATA_IN. Other encoding techniques are also possible.

A message is transmitted back to the planet 100 by way of the DATA_OUT line being toggled between the NEG and POS voltage levels. When transitioning to POS, transistor Q3 is switched on which in turn activates a modified Clapp oscillator comprising Q1, Q2, C1, C4, R1 and R2. Capacitors C1 and C4 preferably tune the antenna coil L1 to a frequency other than that used for incoming energy/communication from the planet. Thus, the positive-going pulses at DATA_OUT cause pulse-modulated bursts of RF energy across the antenna coil by way of capacitor C2. Timing between bursts may be encoded with data to be sent to the planet.

Referring now to FIGS. 5 and 16, the stimulus storage unit 206 stores electrical energy provided to it by the pump-regulator 230 via the POS and NEG voltages lines. The stimulus storage unit 206 preferably includes capacitor C7 which is charged by a current from the pump-regulator 230 via the POS and NEG voltage lines. The electrical energy retained by capacitor C7 can be delivered to the cardiac tissue via electrodes 202 and 203 through capacitor C8.

The stimulus storage 206 preferably is activated to deliver the stored energy upon receipt of a control signal (DATA_IN) from the transceiver 222 to the receiver data decoder/encoder 218. As shown, receiver data decoder/encoder 218 preferably includes a decoder 284 and a one-shot circuit 286. An encoder is also included as part of decoder/encoder 218 but is not shown in FIG. 16 for sake of clarity. The data decoder 284 continuously compares the incoming data with a preset number of code bits (e.g., a nybble) and outputs a trigger signal to the one-shot circuit 286 when the incoming code on the DATA_IN signal matches the preset code. In response, the one-shot 286 provides a single voltage pulse which opens solid state switch SW1. Switch SW1 previously was closed to permit the pump-regulator 230 to charge capacitor C7 to approximately the full POS voltage with respect to NEG.

At substantially the same time that SW1 opens, the single pulse from one-shot 286 closes switch SW2 to permit capacitor C7 to discharge through capacitor C8, through electrode 203, through the cardiac tissue, and back through electrode 202. The resistor R7 discharges any charge built up on capacitor C8 when the one-shot output pulse returns to its quiescent state. At that point, switch SW1 is closed to charge capacitor C7 and switch SW2 is opened.

Referring again to FIG. 5, the satellite 200 also monitors the electrical activity of the heart by processing the electrical voltage across the electrodes 202 by the sensing amplifier and comparator 210. Amplifier and comparator 210 preferably suppresses electrode artefacts, such as time and temperature varying polarization potentials. The processing performed by the amplifier and comparator circuit 210 generally includes amplification, filtering, and comparing the amplified and filtered voltage to a threshold voltage generated internal to the satellite. The input signal to the sensing amplifier and comparator circuit 210 is a differential input connection between the electrodes 202, 203. Alternatively, a separate electrode or pair of electrodes (not shown) may be used for sensing remotely from electrodes 202 that are used for pacing.

Referring now to FIG. 17, amplifier and comparator 210 preferably includes three high pass filters (HPF) 288, 290, 292, two amplifiers 289, 291, and comparator 293, although numerous other architectures and implementations are possible. For example, circuit 210 can be implemented as a single filter and single amplifier. Each high pass filter preferably is implemented as a one or two pole, analog filter. The frequency response of each filter may be the same or different from the other filters. The gain of amplifiers 289, 291 preferably is set at 32, although other gain settings may be acceptable. The sensing amplifier and comparator 210 preferably is a linear (i.e., continuous time), low-power circuit. Alternatively, the amplifier and comparator 210 may be implemented as a switched capacitor design used to further minimize power consumption. An exemplary amplifier, comparator and filter is described in U.S. Pat. No. 4,880,004, assigned to Sulzer Intermedics, and incorporated herein by reference.

The output signal from HPF 292 is compared to a reference voltage $V_{REF}$ by comparator 293 which asserts an output signal if the HPF 292 signal exceeds the $V_{REF}$ threshold. The reference voltage $V_{REF}$ is set at a level such that voltages greater than $V_{REF}$ indicate the presence of sense events while voltages less than $V_{REF}$ indicate the absence of sense events. Thus, an asserted comparator 293 output signal indicates the occurrence of a cardiac sense event at the site of the satellite. The comparator 293 may also be a window comparator which outputs a signal when the amplified sense events exceed $+V_{REF}$ or $-V_{REF}$.

Referring again to FIG. 5, the amplifier and comparator 210 provides a digital signal indicative of the presence or absence of a sense event to the sense event state interface 214. When the sense event state storage interface receives this digital signal, it provides an identifier signal to the receiver data decoder/encoder 218 which, in turn, transmits a signal to the planet 100 to indicate that the satellite 200 has just detected a sense event. The identifier signal includes a satellite identification code to indicate to the planet which satellite has detected the sense event. The planet preferably receives a signal from every satellite that detects a sense event.

Preferably, each command that is received by the satellite 200 is decoded by the receiver data decoder/encoder 218. Upon receipt of a valid command from the planet 100, the receiver data encoder/decoder 218 provides a confirmation signal to the planet confirming that the satellite is functional and communicating. The confirmation signal can be provided to the planet by either affirmatively transmitting back a confirmation signal, or affecting the incoming energy in such a way to permit the planet to detect such a change.

The pacer network 80 can be configured to permit a variety of different commands to be communicated from the planet to the satellites. For example, the planet 100 may command a satellite 200 to deliver the electrical energy stored in the stimulus storage unit 206 to the electrodes 202, 203 (i.e. "pace" the heart). Additionally, the planet 100 may command a satellite 200 to transmit to the planet the data stored in the sense event state storage interface 214. Command messages communicated by the planet 100 are retrieved by the data encoder/decoder 218 which converts the commands into semiconductor switch control voltages. The switch control voltages either cause the sense event state storage interface 214 to convey its data to the encoder/decoder 218 or cause the stimulus storage unit 206 to convey energy to the heart as a pulse of voltage between the two electrodes 202, depicted as circles in FIG. 5.

Figure 6:
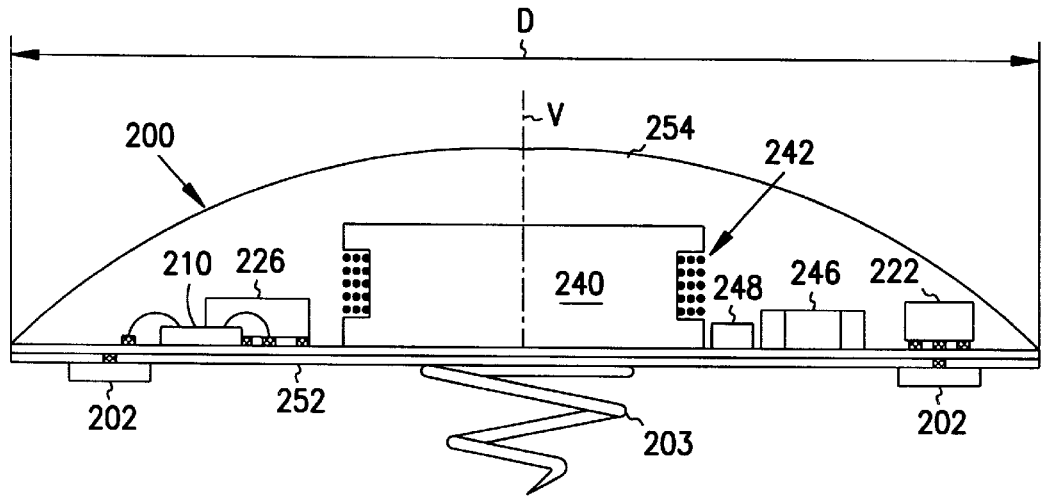
FIG. 6 is a cross-sectional view of a satellite showing one embodiment for attaching the satellite to a human heart.

Referring now to FIG. 6, a single satellite 200 is shown in a crosssectional view. The satellites preferably are circular as viewed along vertical axis V. As such, the diameter D of the satellites preferably is approximately eight millimeters or less. If desired, the satellites may be formed into other shapes and sizes.

The components of each satellite 200 preferably are mounted on a biocompatible substrate 252, formed from a suitable material such as aluminum oxide ceramic. Because FIG. 6 depicts a cross-sectional view of the arrangement of the components in a satellite, not all of the components from FIG. 5 are shown in FIG. 6. Those components that are shown include electrodes 202 and 203, amplifier and comparator 210, and pump rectifier 226. The antenna 223 in FIG. 5 is represented in FIG. 6 as a coil of wire 242 wrapped around a core 240 (preferably a ferrite core). The RF capacitors 248 and transceiver 222 tune the satellites to optimally receive the electromagnetic signal transmitted by the planet. Other communication techniques can be implemented besides RF communication. For example, communication by way of sonic energy is possible. As such, the RF coil can be replaced with a piezoelectric transducer to receive the sonic energy from the planet.

Referring still to FIG. 6, electrodes 202 and 203 project downward from the bottom surface 252. Electrode 202 preferably is an annular electrode. Electrode 203 serves two functions. One function is as an electrode for electrically coupling the satellite 200 to the heart for detecting sense events as well as for conducting electrical pulses to the heart for pacing therapy. The other function performed by the electrode 203 is to be an attachment mechanism to permit the satellite 200 to be attached to the lining of the heart. As shown, electrode 203 is shaped like a spiral or corkscrew, although the electrode can be shaped in any manner desired for attaching the satellite to the heart. If shaped like a corkscrew, the satellite 200 is attached to the cardiac tissue by rotating the satellite, thereby screwing the electrode into the cardiac tissue. Accordingly, if the satellite is implanted thoracoscopically, the satellite is attached to the heart by rotating through the thoracoscopic instrument during implantation.

Figure 7:
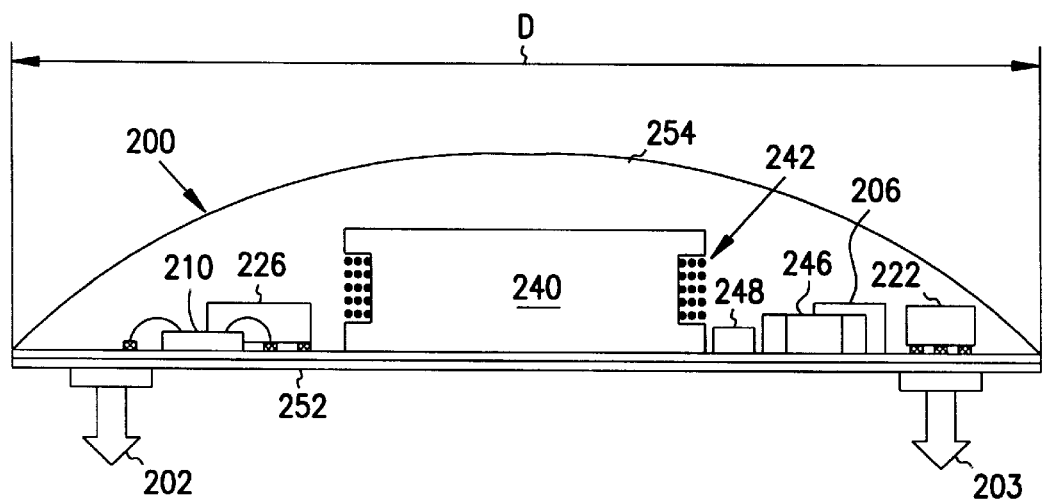
FIG. 7 is a cross-sectional view of a satellite showing an alternative embodiment for attaching the satellite to a human heart.

An alternative embodiment of the attachment mechanism for the satellite 200 is depicted in FIG. 7 in which electrodes 202 and 203 are constructed as barbed electrodes that are pushed into the cardiac tissue, rather than screwed in as in FIG. 6. Preferably, the barbed electrodes 202 and 203 are flexible to minimize potential damage to the heart over repeated contractions and expansions of the cardiac tissue beneath the satellite.

Figure 14:
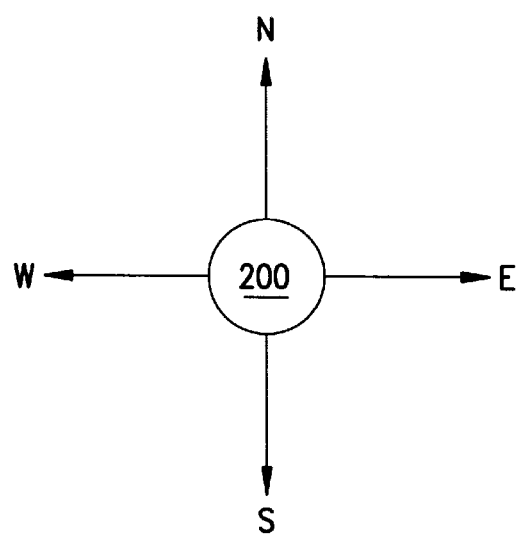
FIG. 14 shows a top schematic view of a satellite.

Both the corkscrew configuration (FIG. 6) and the barbed configuration (FIG. 7) may have more than two periphery electrodes in order to sense depolarization wavefronts arriving from all possible directions in the plane of the satellite base 252. Furthermore, the polarity of the voltage detected between the electrodes may be encoded and transmitted to the planet, to be interpreted as an arrival direction. For example, referring to FIGS. 6, 7, and 14 the satellites may be viewed from above along axis V and superimposed with the compass points: North, South, East, and West. As such, when a wavefront comes from the North, the polarity of the voltage on the electrodes will discriminate this arrival direction from a wavefront of the same magnitude arriving from the South.

Referring still to FIG. 6 and 7, it is important to encapsulate the satellites to protect the satellite's components from body fluids. The encapsulate material for the satellites preferably is a biocompatible, non-porous material such as a ceramic. The encapsulant alternatively may comprise a high resistivity, biocompatible metal such as titanium so as to admit radio frequency energy with little attenuation thereby permitting direct pickup of energy in the RF coil 242. Alternatively, the encapsulant could be inside a metal enclosure of any resistivity, provided the RF energy enters the satellite via the electrodes making conductive contact with cardiac tissue.

It is also important to seal the electrodes 202, 203 to prevent body fluids from entering the satellite. Conventional techniques can be used to seal the electrodes. Examples of such techniques are described in U.S. Pat. Nos. 4,152,540; 4,424,551; 5,333,095; 5,406,444; and 5,650,759, incorporated herein by reference.

After the pacemaker network 80 is implanted in the patient, the network preferably is initialized. The purpose of the initialization process is to establish a template of time values that are indicative of the presence of a depolarization wave at each satellite during a normal sinus rhythm cardiac cycle. The planet 100 uses the template to detect and characterize arrhythmias and select an appropriate anti-arrhythmia therapy for the patient.

Figure 8:
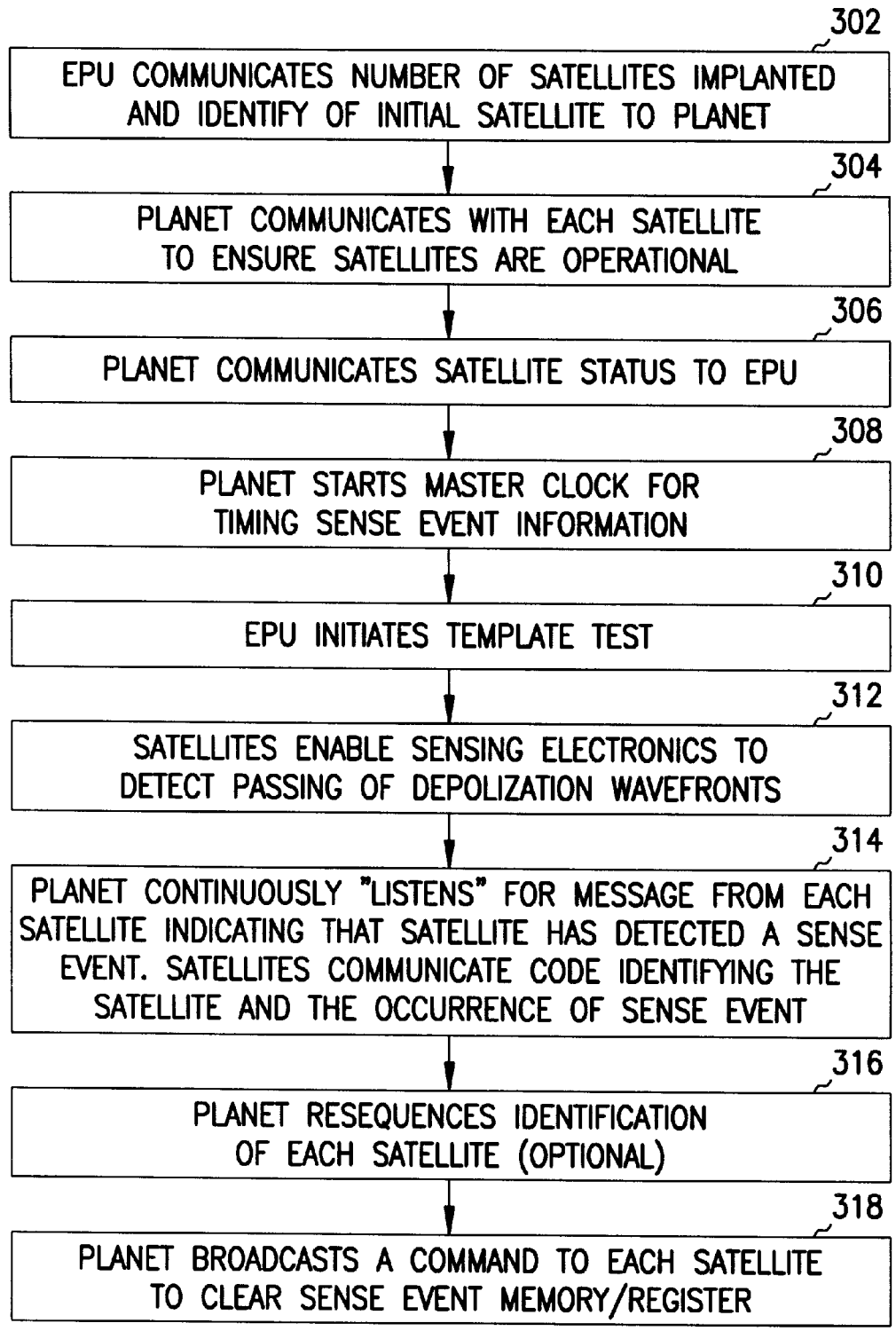
FIG. 8 is a flowchart showing the preferred steps for the operation of an implantable device network of FIG. 1.

Referring now to FIG. 8, an exemplary method including steps 302–318 is shown for initializing the planet 100 and satellites 200 during or after implantation. The following steps preferably are performed while the patient's heart is in normal cardiac rhythm. After the planet 100 and satellites 200 are implanted, the physician uses the EPU 300 (FIG. 1) to communicate the number of satellites that have been implanted to the planet (step 302). The EPU also preferably communicates to the planet which satellite will first detect a depolarization wavefront during a cardiac cycle. This determination is made by the physician using any one or more of a variety of techniques. For example, the EPU 300 can be used to receive sense events directly from the satellites and this information can be shown graphically on a screen (not specifically shown in FIG. 1) included as part of the EPU 300. By superimposing, or otherwise correlating, the sense events to a cardiac cycle, the physician can determine which satellite among the plurality of satellites implanted is the first satellite to detect a depolarization wave during each cardiac cycle. Alternatively, the physician may be able to determine which satellite is the first satellite to detect a depolarization wave merely from knowing the locations on the heart in which the satellites are anchored.

The satellite 100 that first detects the depolarization wave during each cardiac cycle is referred to in this description as the "initial" satellite. The remaining satellites will then detect depolarization waves after the initial satellite detects a depolarization wave. The planet's counter 145 measures the time, from the detection of a sense event by the initial satellite, during a cardiac cycle that each of the other satellites detects a sense event, as will be further explained below. In step 304, the planet communicates with each satellite to ensure that each satellite is operational and reports satellite status to the EPU in step 306. If a satellite does not respond to the planet's attempted communication or responds with an error message, the planet 100 reports these error conditions to the EPU. The physician can use the EPU to interrogate each satellite reported as problematic by the planet.

The planet starts its master clock 143 (FIG. 2) in step 308, if not already started, in response to a command from the EPU 300. The EPU initiates the template test while the patient is in normal cardiac rhythm in step 310 by transmitting a template test start command to the planet 100. Then in response, the planet may transmit a command to each satellite to begin the template test. The satellites then enable their sensing electronics to detect sense events at step 312. Rather then transmitting a command to each satellite to begin the template test, the planet 100 may simply begin communicating with each satellite to power up the electronics in each satellite. The satellites may be configured so that sensing automatically occurs as long as the satellites are activated.

In step 314 once each satellite 200 is operational and sensing depolarization wavefronts, the CPU in the planet 100 waits for a message from each satellite indicating that a satellite has just detected a depolarization wave. Upon receipt of a sense signal from a satellite, the planet's CPU 142 reads the counter 145 and stores a current count value in a table set up in RAM memory 114 to include the template time values. Additionally, the counter time values stored in the template table in the planet may also be transmitted to the EPU before viewing by the physician. Once the physician determines that the template table in the planet contains valid time values for each satellite, the surgeon uses the EPU to transmit a command back to the planet indicating that the planet has successfully initialized the pacer network 80. At this point, the template for the patient's pacer network 80 has been established.

Figure 9:
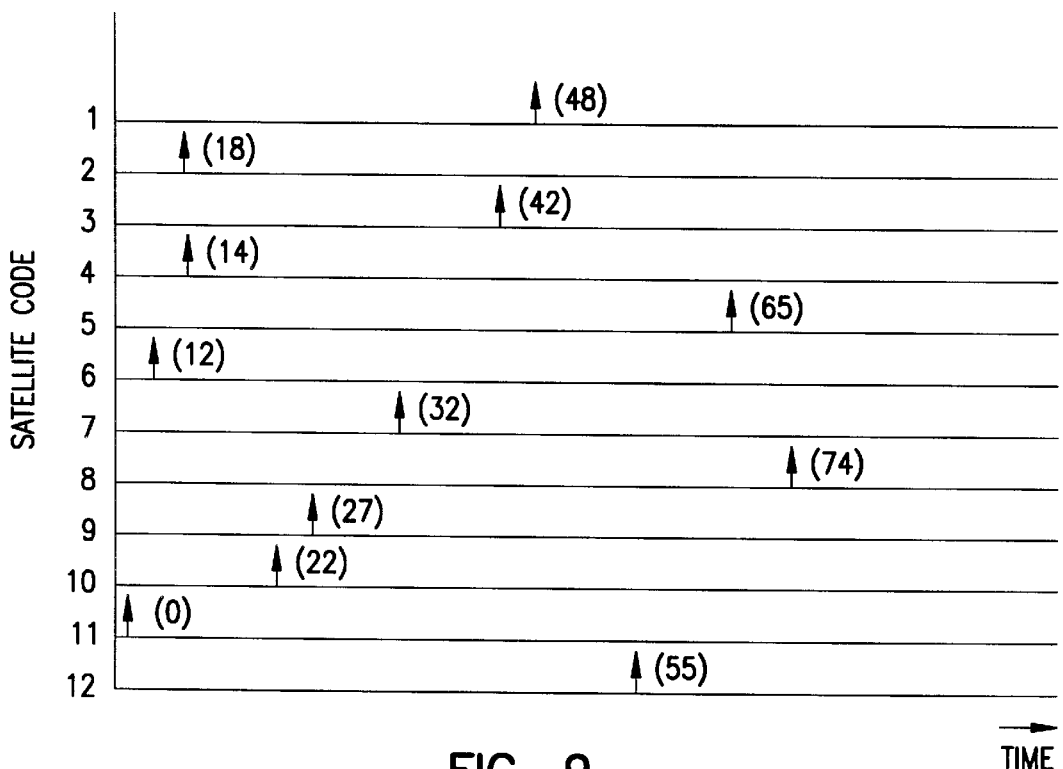
FIG. 9 shows a timeline of the sense events detected by the plurality of satellites in the network of FIG. 1.

Thus, steps 302–314 describe the initialization process for the pacer network 80 that preferably is performed while the patient is experiencing normal sinus rhythm. FIG. 9 shows an exemplary set of time values for the satellites computed by the planet's CPU during the initialization process and which establishes the template for the patient. The "satellite codes" are the unique identification codes assigned to each satellite to permit the planet to communicate individually with each satellite. The vertical arrows indicate the occurrence of a sense event and the numbers in parentheses are the time values assigned by the planet's CPU to each satellite. The time values assigned to each satellite may be the counter's output count value or the count value scaled by a predetermined factor to reflect time measured in units of milliseconds. By "assigning" it is meant that the planet internally associates a value with a satellite, not that the planet necessarily transmits the time value to the satellite. The planet stores the time values in a table in RAM memory 114 wherein each entry in the table corresponds to a unique satellite.

The EPU 300 in the example shown in FIG. 9, reported satellite 11 as the initial satellite, and thus the time value assigned to the sense event reported by satellite 11 is 0 seconds. The time values assigned to the remaining satellites 200 were calculated by counting cycles of the planet's master clock timing signal, beginning with the reporting of a sense event from satellite 11. Thus, the template time values shown in FIG. 9 represent the time occurrence of sense events detected by the network's satellites that have elapsed since initial satellite 11 reported a sense event.

Figure 10:
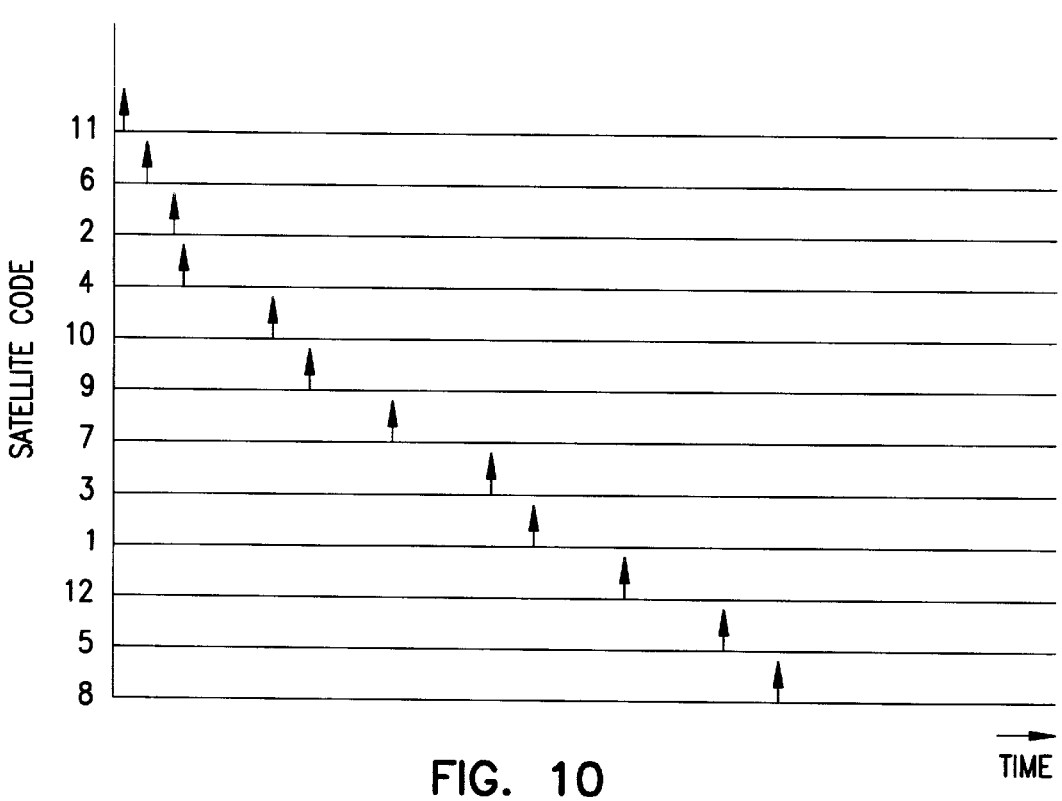
FIG. 10 shows how the planet may reorder the sense event time data shown in FIG. 9.

FIG. 10 shows the template timing data of FIG. 9 reordered in sequence from the initial satellite 11 to the last satellite (satellite 8) that detects a sense event during a cardiac cycle. By resequencing the template timing data in the order shown in FIG. 10, the order of the satellites in which the satellites detect depolarization wavefronts propagating through the cardiac tissue can be easily seen. As shown in FIG. 10, the depolarization wavefront is detected first by satellite 11, then in order, by satellites 6, 2, 4, 10, 9, 7, 3, 1, 12, 5, and finally satellite 8. The resequencing of the template timing data of FIG. 9 is shown in FIG. 10 primarily for illustrative purposes. It may not be necessary for the planet's CPU 142 to actually reorder the template data by moving the data around in RAM memory 114. However, if desired, and as shown in optional step 316 in FIG. 8, the planet's CPU 142 may reorder the template timing data of FIG. 9 in accordance with FIG. 10.

Once the template for the patient is established and stored in the planet's RAM memory 114, the planet broadcasts a command to each satellite to clear the satellite's sense event state interface 214 so that the satellites are prepared to detect new sense events. The planet also commands a satellite 200 to clear its sense event state interface 214 once that satellite reports the occurrence of a sense event to the planet. The pacer network 80 performs steps 302–314 during implantation and preferably during a normal cardiac rhythm. As such, the timing diagram of FIG. 9 (as reordered in FIG. 10) represents a normal template for the patient. In this sense, the timing diagram of FIGS. 9 and 10 are both considered "normal templates." Thus, while the patient is experiencing a normal cardiac rhythm, the planet 100 should assign time values for each satellite that are, within a predetermined range, approximately equal to the template values illustrated in FIGS. 9 and 10.

Following the initialization process depicted in FIG. 8, the pacemaker network begins normal operation. Each time the initial satellite (satellite 11 in the example above) reports the occurrence of a sense event to the planet, the planet's CPU 142 resets counter 145 and assigns a count value of 0 to satellite 11. Then, upon receipt of sense event signals from other satellites in the network, the CPU 142 reads the count value from the counter 145 and assigns a count value for the other satellites. The CPU 142 also compares each assigned satellite count value for a cardiac cycle to the template time value for the corresponding satellite. For example, CPU 142 compares the time value assigned for satellite 6 (the next satellite in the network that should detect a sense event after satellite 11) to the template time value for satellite 6 shown in FIG. 9 (12 milliseconds). This process repeats for each subsequent satellite in the network and if each satellite time value matches its associated template value within a predetermined range or percentage, the planet determines that the patient is experiencing a normal cardiac rhythm.

It is generally recognized that a patient may experience normal cardiac rhythm, but the underlying heart rate can be within a wide range of values. For example, the patient with normal sinus rhythm may experience a 72 beat per minute (BPM) heart rate while at rest, but experience over 100 beats per minute during exercise. Although the patient may be in normal cardiac rhythm in both situations, the patient's heart rate and thus the timing associated with the detection of sense events by each satellite will be dramatically different. To account for such variations in the patient's heart rate, the planet may be incorporated with a sensor 106 as shown in FIG. 2. This sensor preferably is a general body activity sensor, such as an accelerometer commonly used in pacemaker configurations. This sensor provides an output signal to the CPU 142 that it is indicative of the patient's overall body activity. The CPU 142 can interpret the signal from the sensor and generally determine whether the patient is exercising or is at rest. The planet 100 can be configured with one or more multiplier values that are stored in ROM memory 110 and used by the CPU 142 to process the sense signals from the satellites. For example, if the CPU 142 in the planet determines that the patient is experiencing a high level of exercise, the CPU can use an appropriate multiplier value to adjust the count values read from the counter 145. That appropriate multiplier value might be, for example, a factor of 2, such that any count value read from the counter would be multiplied by 2 before comparison with the normal sinus rhythm template. In this way, the patient's normal sinus rhythm template, which will be set while the patient is at rest and experiencing a relatively low heart rate, can be used for comparison with the patient's satellite timing data even though the patient is experiencing a substantially different heart rate, albeit still during normal sinus rhythm. The multiplier values preferably are determined before implantation during a stress test or other suitable cardiovascular test, and are programmed into the planet 100, along with the range of time values or percentage range that will be considered by the planet as matching the template.

Figure 11:
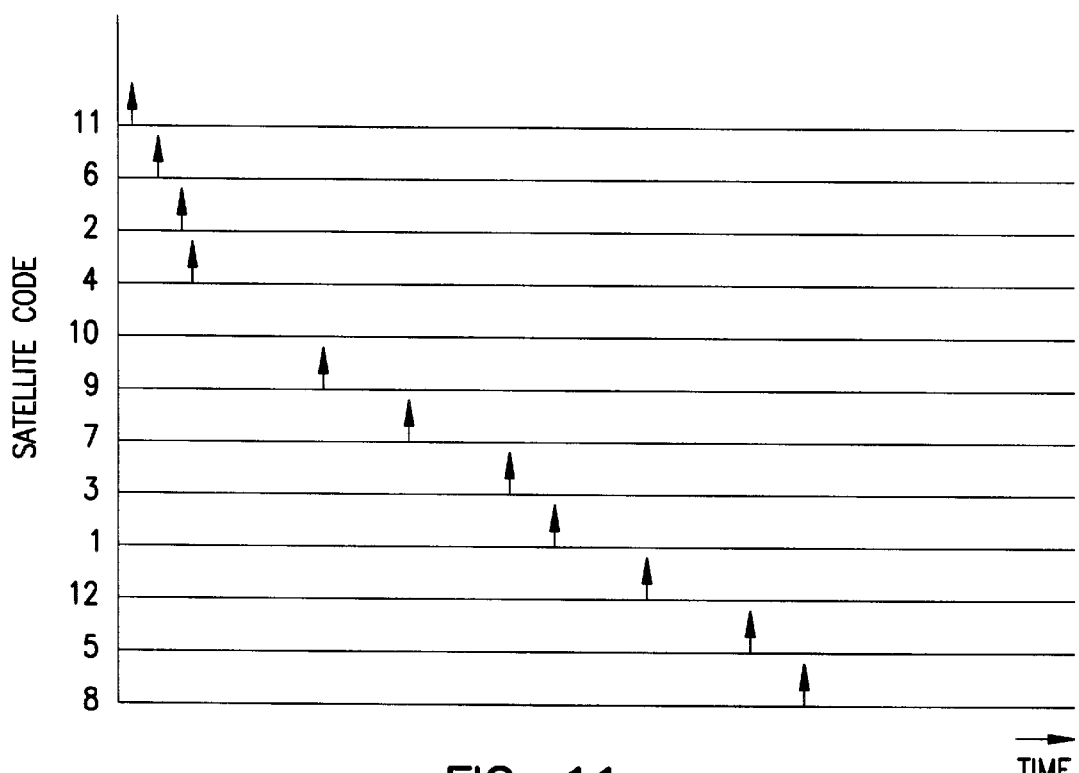
FIG. 11 shows satellite sense event time data received by the planet during a bradycardic condition.
Figure 12:
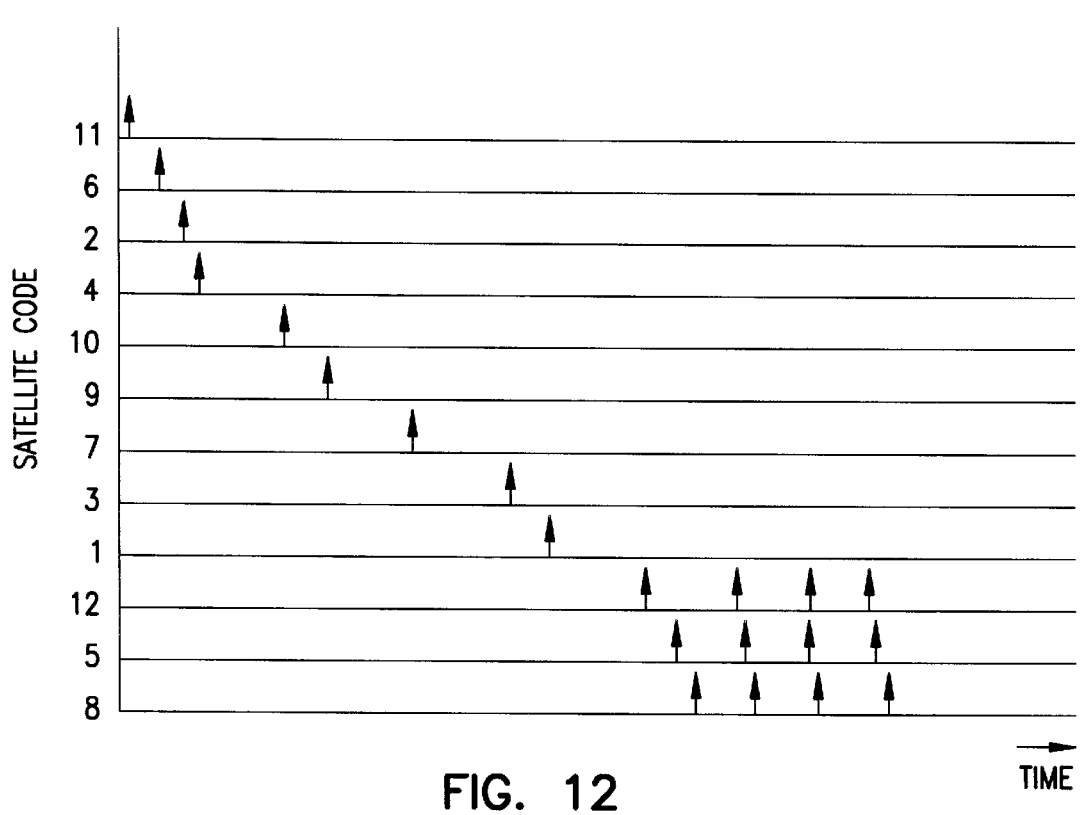
FIG. 12 shows satellite sense event time data received by the planet during a tachycardic condition.
Figure 13:
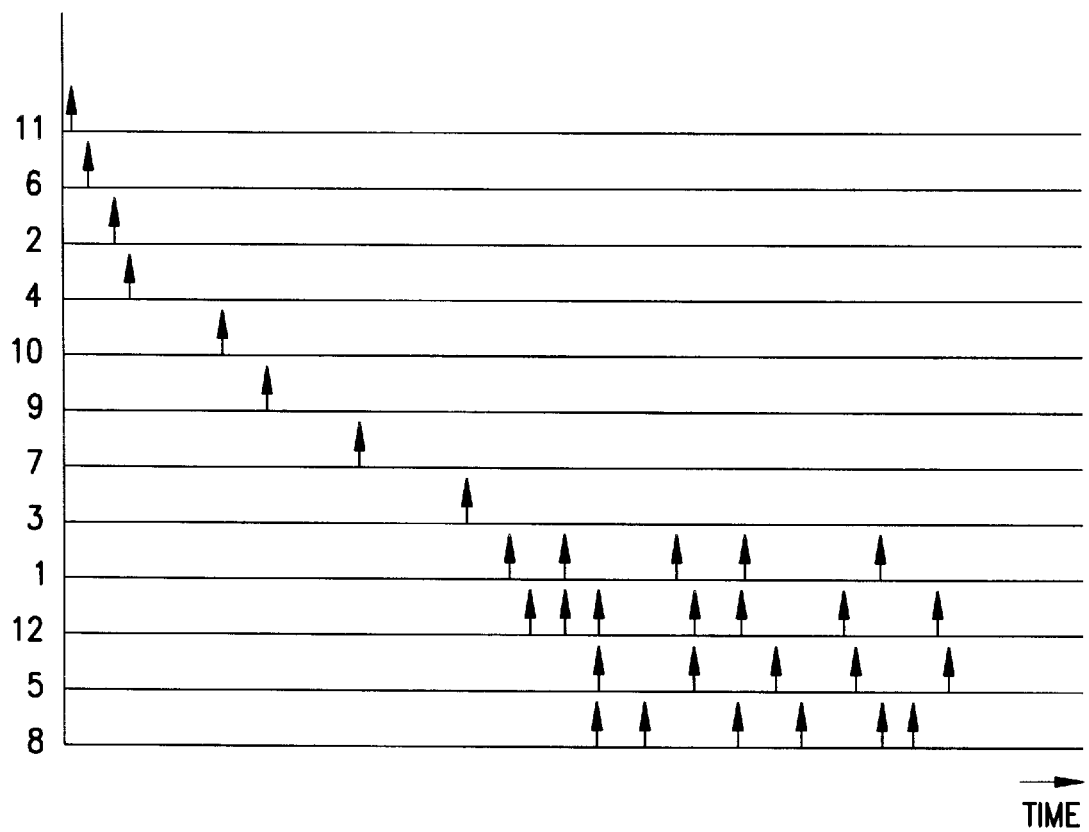
FIG. 13 shows satellite sense event time data received by the planet during a fibrillation condition.

If, however, the time value for a satellite 200 does not match the template value, within the predetermined range or percentage of values, or if the planet 100 does not receive a signal from a satellite 200 indicating the occurrence of a sense event, the planet determines that an abnormal condition has occurred and responds appropriately. The planet may determine that the patient is experiencing an arrhythmia and, if so, the planet will attempt to implement a suitable anti-arrhythmia therapy for the patient. FIGS. 11–13 illustrate three types of arrhythmias detectable by the planet—bradycardia (FIG. 11), tachycardia (FIG. 12), and fibrillation (FIG. 13).

Referring now to FIG. 11, a bradycardic patient may exhibit abnormally delayed sense events or a complete absence of sense events at certain locations in the heart. As shown in the example of FIG. 11, satellite 10 never detected a sense event and thus, the CPU 142 never assigned a time value to satellite 10 during that cardiac cycle. If the patient's problem is loss of electrical conduction close to satellite 10, then propagation times between consecutive satellites may be unaffected. The bradycardic condition illustrated in FIG. 11 is an idealized situation, but the timing diagram serves to show that one missed sense event can be confirmed by detecting sense events by satellites further along the conductive pathway (e.g. satellites 9, 7, and 3 in FIG. 11). The planet 100 can reduce the possibility of a false negative sense event, such as might occur due to an error in the satellite or motion artifact disturbing sensing, by monitoring the time values for the other satellites located closest to satellite 10. If the other satellites adjacent to satellite 10 indicate that sense event timing is still within a predetermined range, specific to those other satellites, the planet 100 will determine that the absence of a sense event at satellite 10 was not a true indicator of an arrhythmia. Confirmation of a false negative event at satellite 10 may also be performed by commanding satellite 10 to stimulate tissue during the time period when it would normally expect a sense event in a subsequent cardiac cycle. If that produces a normalization of sense event timing at adjacent satellites then the previous absence of an event at satellite 10 may be attributed to an arrhythmia (loss of conduction).

If the planet, however, determines that the missing sense event from satellite 10 was due to a true bradycardic condition, the planet preferably selects a suitable pacing therapy to combat the condition. A suitable therapy would be for the planet to command satellite 10 to stimulate the cardiac tissue at the site of satellite 10 during the time slot when a sense event normally should occur for satellite 10. The planet determines when satellite 10 should normally detect a sense event from the normal sinus rhythm template (FIGS. 9 and 10).

By way of another example, a tachycardic patient may exhibit several sense events per cardiac cycle at one or more satellites due to a "circus" motion of wavefront depolarization. That is, several events may be detected by one satellite for every one event detected by another satellite. FIG. 12 shows a satellite timing example of a patient experiencing tachycardia in the region of the heart in which satellites 5, 8, and 12 are anchored. The planet's CPU 142 detects this condition by comparing the assigned time values in FIG. 12 with the template from FIG. 10. An appropriate therapy selected by the planet to combat this condition may be for the planet to command satellite 12 to stimulate the cardiac tissue in advance of the second sense event in a subsequent cardiac cycle. In principle, a new depolarization wavefront would be generated to eliminate the circus motion by rendering the tissue refractory (i.e., unable to be restimulated), without regenerating another circus motion in the process. Satellites 5 and 8 may act in concert if they exist in the same circus loop and stimulate simultaneously to break the tachycardic condition.

The pacemaker network 80 can also be used to detect and treat fibrillation, another type of arrhythmia. During fibrillation, sections of conductive cardiac tissue of the affected chamber undergo completely uncoordinated, random contractions, quickly resulting in a loss of the blood-pumping capability of that chamber. During ventricular fibrillation (i.e., fibrillation occurring in a ventricular chamber), cardiac output ceases instantaneously. Unless cardiac output is restored almost immediately after the onset of ventricular fibrillation, tissue begins to die for lack of oxygenated blood, and death of the patient will occur within minutes.

The onset of a life-threatening fibrillation condition is illustrated in FIG. 13. In this example, propagation through satellites 11, 6, 2, 4, 10, 9, 7, and 3 is normal, but chaotic rotor motion causes satellites 1, 12, 5, and 8 to detect multiple sense events in a random manner as shown. This fibrillation condition is detected by the planet's CPU 142 by comparison of the time values assigned to each satellite with the template. In response, the planet 100 selects a pacing therapy, such as that described in U.S. Pat. No. 5,342,401, incorporated herein by reference, to terminate the fibrillation by stabilizing the chaotic system and reducing it to a treatable tachycardia. The therapy selected advantageously permits pacing level voltages (less than approximately 3 volts) to be applied by the satellites to the heart, rather than the relatively large voltages (on the order of 700 volts) typically generated by implantable defibrillators that deliver their energy to the heart via leads.

There are numerous benefits and advantages to the preferred embodiment of the invention, such as:

(1) The absence of leads placed within the heart avoids problems of scarring, adhesion to valve leaflets, endocarditis, thrombus formation, endocardial cushion lesions, mineralization in and erosion of the myocardium which are known to occur to varying degrees over the lifetime of present day implantable stimulus leads;

(2) Numerous sensing locations enable mapping of the propagation of myocardial cell depolarization and the identification of regions of electrical insufficiency;

(3) A multiplicity of stimulus locations also permits spatially-coordinated pacing energy stimulation in the treatment of symptoms of bradycardia, tachycardia and fibrillation;

(4) Without leads, surgically removing the pacer network as may be desirable or necessary at some time subsequent to implantation is not made difficult by fibrotic tissue that accrues gradually around a lead;

(5) The satellites can be relatively easily implanted by means of known surgical techniques, including thoracoscopic techniques, which do not involving traversing veins;

(6) Communication with an external programmer does not require an extra interface, such as a coil commonly used in present day ICD's and pacemakers;

(7) An epicardial ECG will be available to an external programmer simultaneous with interrogation of the planet, or independent of the planet and may eliminate the need for surface electrodes applied to the patient's body;

(8) The satellites may be applied at the time of surgery in adults or infants as a prophylactic measure, for a future time when electrical therapy may be needed;

(9) Placement of satellites at the time when surgery permits some electrophysiological evaluation of the patient in the absence of any catheter placement in diseased hearts. Without the planet, interrogation of the satellites by means of an external programmer would provide diagnostic information prior to or during electrical and/or pharmacological therapy;

(10) The satellites, having no batteries, minimize or eliminate the risk of the leakage of toxic contaminants into surrounding tissue;

(11) A rechargeable version of the planet would offer extended life to the pacer network 80 without the need to extract or replace leads; and

(12) The integrity of a complete planet-satellite system is not jeopardized by a malfunction of any one satellite. A malfunctioning satellite may be explanted (i.e., removed) or left implanted, adjacent to a replacement satellite.

Numerous variations and modifications will become apparent to those skilled in the art once the above disclosure is fully appreciated. It is intended that the following claims be interpreted to embrace all such variations and modifications.

What is claimed:

1. An implantable medical device for attachment to human tissue, comprising:

a plurality of electrodes for connection to the tissue;

a communications device for receiving signals and energy via a wireless communication path from a control device;

a stimulus storage device coupled to said communications device and said electrodes for receiving electrical energy from said communications device to be stored and delivered to the tissue through the electrodes;

a rectifier disposed between said communications device and said stimulus storage device for rectifying said signals received from said control device;

a regulator disposed between said rectifier and said stimulus storage device for regulating the rectified signal from said rectifier; and a receiver data decoder/encoder having a data encoder for producing encoded wireless communication signals identifying said implantable medical device and for conveying data.

2. The implantable medical device of claim 1 wherein said communications device includes an antenna.

3. The implantable medical device of claim 1 wherein all of the electrical energy needed to operate the medical device is obtained from the wireless communication signals received by the communications device.

4. The implantable medical device of claim 1 wherein said receiver data decoder/encoder further has a data decoder for decoding the wireless communication signals received by the communications device.

5. The implantable medical device of claim 4 wherein said receiver data decoder/encoder commands said stimulus storage device to deliver said stored electrical energy to said electrodes upon decoding a signal from the communications device indicating that at least part of the stored energy should be delivered to the electrodes.

6. The implantable medical device of claim 1 wherein said electrodes include a barbed projection for attaching said medical device to said tissue.

7. The implantable medical device of claim 1 wherein said electrodes include a spiral projection for attaching said medical device to said tissue.

8. The implantable medical device of claim 1 wherein said electrodes include a means for attaching said medical device to said tissue.

9. The implantable medical device of claim 1 wherein said medical device is approximately circular in cross section with a diameter of less than approximately 8 millimeters.

10. An implantable medical device for attachment to human tissue, comprising:

a plurality of electrodes for connection to the tissue;

a communications device for receiving signals and energy via a wireless communication path from a control device, wherein said communications device includes a transducer to convert non-electromagnetic energy to electrical energy;

a stimulus storage device coupled to said communications device and said electrodes for receiving electrical energy from said communications device to be stored and delivered to the tissue through the electrodes;

a rectifier disposed between said communications device and said stimulus storage device for rectifying said signals received from said control device; and a regulator disposed between said rectifier and said stimulus storage device for regulating the rectified signal from said rectifier.

11. An implantable medical device for attachment to human tissue, comprising:

a plurality of electrodes for connection to the tissue;

a communications device for receiving signals and energy via a wireless communication path from a control device, wherein said communications device includes an antenna and wherein said antenna includes a direction of highest energy radiation per unit solid angle that is not co-axial with a longitudinal axis of the antenna;

a stimulus storage device coupled to said communications device and said electrodes for receiving electrical energy from said communications device to be stored and delivered to the tissue through the electrodes;

a rectifier disposed between said communications device and said stimulus storage device for rectifying said signals received from said control device; and a regulator disposed between said rectifier and said stimulus storage device for regulating the rectified signal from said rectifier.

12. An implantable medical device for attachment to human tissue, comprising:

a plurality of electrodes for connection to the tissue;

a communications device for receiving signals and energy via a wireless communication path from a control device;

a stimulus storage device coupled to said communications device and said electrodes for receiving electrical energy from said communications device to be stored and delivered to the tissue through the electrodes;

a rectifier disposed between said communications device and said stimulus storage device for rectifying said signals received from said control device;

a regulator disposed between said rectifier and said stimulus storage device for regulating the rectified signal from said rectifier; and a rechargeable battery, wherein at least part of the electrical energy received by said communications device is delivered to said battery.

13. An implantable medical device for attachment to human tissue, comprising:

a plurality of electrodes for connection to the tissue;

a communications device for receiving signals and energy via a wireless communication path from a control device;

a stimulus storage device coupled to said communications device and said electrodes for receiving electrical energy from said communications device to be stored and delivered to the tissue through the electrodes;

a rectifier disposed between said communications device and said stimulus storage device for rectifying said signals received from said control device;

a regulator disposed between said rectifier and said stimulus storage device for regulating the rectified signal from said rectifier; and a sense amplifier and comparator coupled to said electrodes for amplifying electrical signals generated by said tissue and comparing said amplified signal to a reference signal to verify that a sense event has occurred.

14. The implantable medical device of claim 13 further including a sense event state interface coupled to said amplifier and comparator and a receiver data decoder/encoder to provide an identifying signal indicating the occurrence of a sense event.

15. The implantable medical device of claim 14 wherein said communications device receives an indication from said sense event state interface of a sense event and said communications device transmits via a wireless communications path to said processing device a signal indicating the occurrence of a sense event.

16. The implantable medical device of claim 13 further including a means for communicating the occurrence of said sense event via a wireless communication path to a processing device.

17. A planet medical device for controlling a plurality of satellite implantable medical devices, comprising:

a processor for interpreting signals received from the plurality of satellite devices;

a memory device coupled to said processor;

a communications device coupled to said processor for receiving signals from and transmitting signals to said plurality of satellite devices;

a battery for providing electrical power to said processor, memory device, communications device, and said satellite devices; and a clock providing a periodic timing signal to said processor for assigning time values to sense events reported by each satellite device.

18. The planet device of claim 17 further including a receiver data decoder disposed between said communications device and said processor for decoding signals received from said satellites via said communications device and providing said decoded signals to said processor.

19. The planet device of claim 18 wherein said receiver data decoder is capable of decoding signals from said satellites as sense events.

20. The planet device of claim 19 further including a counter for counting cycles of said periodic timing signal and providing a count value to said processor.

21. The planet device of claim 20 wherein said processor resets or latches the output of said counter upon receipt of a wireless sense event signal from a planet.

22. The planet device of claim 20 wherein said processor latches an output signal from said counter upon receipt of a wireless sense event signal from a planet.

23. The planet device of claim 21 wherein said planet that causes said processor to reset said counter is an initial satellite and said processor assigns a count value to each of the other satellites upon receipt of a sense event signal from the other satellites.

24. The planet device of claim 23 wherein said processor compares said assigned count values to a template of normal count values to determine if an anomalous condition has occurred.

25. The planet device of claim 24 wherein said planet device is adapted to be used in conjunction with satellites attached to a human heart and said template of normal count values represents the count values for the patient during a normal cardiac rhythm.

26. The planet device of claim 17 wherein said planet device is implantable into a human body.

27. A planet medical device for controlling a plurality of satellite devices, comprising:
   a processor for initiating timing signals to be communicated to said satellite devices;
   a memory device coupled to said processor;
   a communications device coupled to said processor for receiving signals from and transmitting signals to said plurality of satellite devices; and
   a battery for providing electrical power to said processor, memory device, communications device, and said satellite devices.

28. A medical system for monitoring and stimulating the heart to beat, comprising:
   a planet control device, including;
      a processor;
      a memory device coupled to said processor;
      a planet communications device coupled to said processor for receiving and transmitting signals using a wireless communications technique; and
      a battery for providing electrical power to said processor, memory device, and communications device; and
   a plurality of satellite sensing and stimulating devices, each satellite including;
      a plurality of electrodes for connection to the heart;
      a satellite communications device for receiving signals from and transmitting signals to said communications device in said planet control device via said wireless communication technique;
      a rectifier coupled to said satellite communications device to derive operational electrical power needed by the satellite from the signals received by said satellite communications device wirelessly transmitted by said planet communications device; and
      a regulator coupled to said rectifier for regulating the rectified signal from said rectifier.

29. The medical system of claim 28 wherein the electrodes of said satellites include projections to permit the satellites to be attached to an exterior surface of the heart.

30. The medical system of claim 28 wherein said satellites include a stimulus storage device disposed between said rectifier and said electrodes for storing electrical charge to be subsequently delivered to the heart via the electrodes to stimulate the depolarization of cardiac tissue.

31. The medical system of claim 28 wherein said satellites further include a sense amplifier and comparator coupled to said electrodes and said satellite communications device to process signals detected by said electrodes, compare said signals with a reference signal and provide an indicator signal to said communications device that a sense event has occurred.

32. The medical system of claim 31 wherein said satellite includes a receiver data decoder/encoder having a data encoder and disposed between said sense amplifier and comparator and said satellite communications device to generate an encoded signal to be wireless transmitted to said planet communications device via said satellite communications device to indicate that a sense event has occurred.

33. The medical system of claim 32 wherein said receiver data decoder/encoder also encodes a satellite identifier into said encoded signal.

34. The medical system of claim 33 wherein said planet also includes a clock for providing a periodic timing signal and a counter for receiving said timing signal and producing an output count value indicative of the number of cycles of said timing signal counted by said counter.

35. The medical system of claim 34 wherein said processor reads said count values from said counter and assigns said count values to a satellite upon receipt of an encoded signal from that satellite that a sense event has occurred.

36. The medical system of claim 35 wherein said processor resets or latches the output of said counter upon receipt of an encoded signal from a predetermined satellite that a sense event has occurred.

37. A method for implanting and initializing an implantable leadless medical system, comprising:
   attaching a plurality of satellite devices to the heart;
   communicating the number of implanted satellite devices to a central control unit;
   communicating the identity of a first satellite device that will first detect a sense event during each cardiac cycle to the central control unit; and
   storing the identity of said first satellite device in memory and said central control unit.

38. The method of claim 37 further including establishing a communication link between said central control unit and each of said satellite devices to ensure each satellite device is operational.

39. The method of claim 37 further including detecting sense events by the satellite devices while the patient is experiencing normal cardiac rhythm and transmitting signals that indicate the occurrence of sense events to the central control device.

40. The method of claim 39 further including resetting or latching the output of a counter upon receipt of a signal indicating the occurrence of a sense event from the first satellite device.

41. The method of claim 40 further including assigning a count value to all other satellite devices that transmit signals indicating the occurrence of a sense event.

42. The method of claim 41 wherein said assigned count values comprise a template and storing said assigned count values in memory and said central control device.

43. A method for pacing and sensing a human heart using an apparatus that includes a plurality of implantable satellites attached to the heart and a planet control device that communicates with said satellites via a wireless transmission link, said method comprising:
   receiving signals indicating the occurrence of sense events from said satellites;
   assigning time values to said satellites upon receipt by said planet of said sense event signals;
   comparing said time values to a template of time values;
   determining that an arrhythmia has occurred if said time values do not match said template within a predetermined tolerance; and
   communicating the times at which one or more satellites should stimulate cardiac tissue to correct the arrhythmia.

* * * * *